(12) United States Patent
Weatherbee

(10) Patent No.: US 7,758,492 B2
(45) Date of Patent: *Jul. 20, 2010

(54) PULSATILE BLOOD PUMPING SYSTEMS

(76) Inventor: Paul Weatherbee, 4025 Cougar Way, Abilene, TX (US) 79606-2329

(*) Notice: Subject to any disclaimer, the term of this patent is extended or adjusted under 35 U.S.C. 154(b) by 1201 days.

This patent is subject to a terminal disclaimer.

(21) Appl. No.: 11/347,977

(22) Filed: Feb. 6, 2006

(65) Prior Publication Data

US 2006/0129023 A1 Jun. 15, 2006

Related U.S. Application Data

(63) Continuation of application No. 10/824,821, filed on Apr. 15, 2004, now Pat. No. 7,014,605.

(51) Int. Cl.
*A61M 1/10* (2006.01)
(52) U.S. Cl. .......................... 600/16; 600/17
(58) Field of Classification Search ............. 600/16–17; 623/3.1, 3.13–3.15, 3.27
See application file for complete search history.

(56) References Cited

U.S. PATENT DOCUMENTS

| 826,985 | A | 7/1906 | Appel |
|---|---|---|---|
| 1,946,343 | A | 2/1934 | Wicha |
| 2,043,544 | A | 6/1936 | Kempthorne |
| 2,708,413 | A | 5/1955 | Loewen |
| 3,492,974 | A | 2/1970 | Kreimeyer |
| 4,600,405 | A | 7/1986 | Zibelin |
| 4,984,972 | A | 1/1991 | Clausen |
| 5,147,193 | A | 9/1992 | Larsen |
| 5,199,864 | A | 4/1993 | Stecklein |
| 5,601,418 | A | 2/1997 | Ohara |
| 5,840,070 | A | 11/1998 | Wampler |
| 6,241,493 | B1 | 6/2001 | Turner |
| 6,527,698 | B1 | 3/2003 | Kung |
| 6,540,658 | B1 | 4/2003 | Fasciano |
| 7,014,605 | B2 * | 3/2006 | Weatherbee ............. 600/16 |

OTHER PUBLICATIONS

Thaddeus Dejesus, "Brothers Apply Pump Design to Oil, Ailing Hearts"., Abilene Reporter-News, Aug. 30, 2003, Abilene, Texas.

* cited by examiner

*Primary Examiner*—Kennedy J Schaetzle
*Assistant Examiner*—Jessica Sarcione
(74) *Attorney, Agent, or Firm*—Michael Ervin; M.A. Ervin & Associates

(57) ABSTRACT

A blood pumping system to support living organisms based on a spherical multi vane and multi chamber pump with an oscillating motion that delivers pulsatile flow. The blood pumping system includes a number of design elements that address the particular needs and compatibility issues (both biological and hemological) of a blood pumping system.

59 Claims, 26 Drawing Sheets

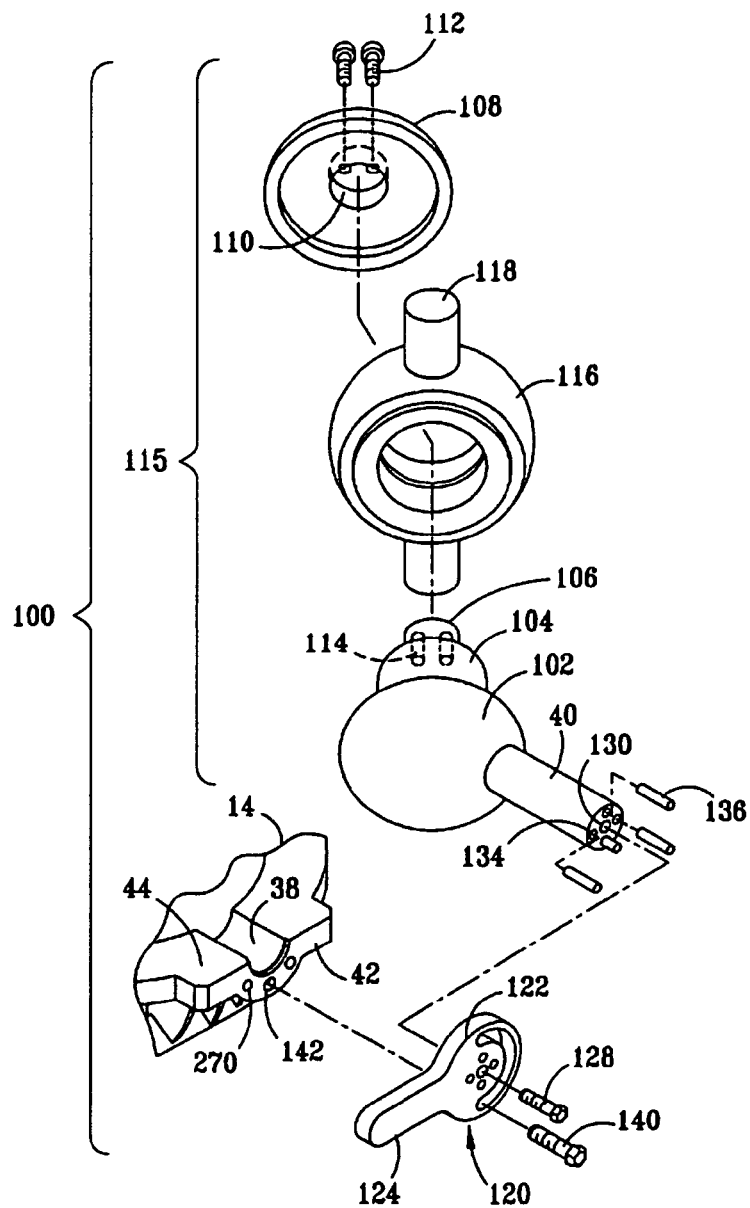
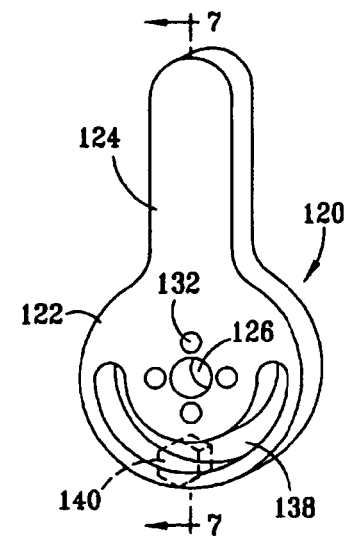
FIG 6
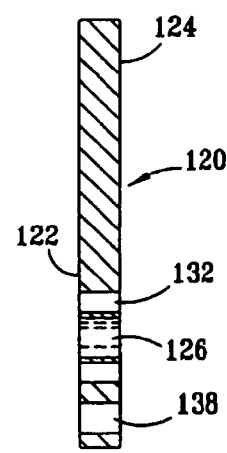
FIG 7
FIG 5

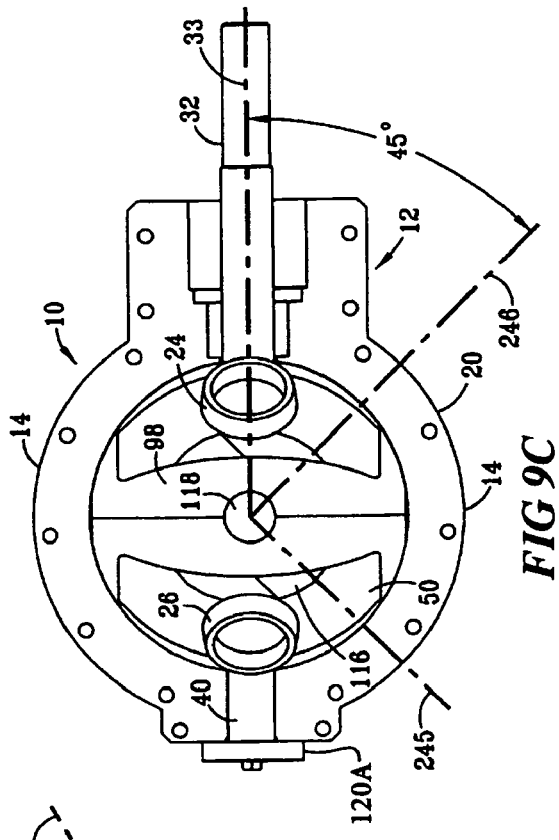
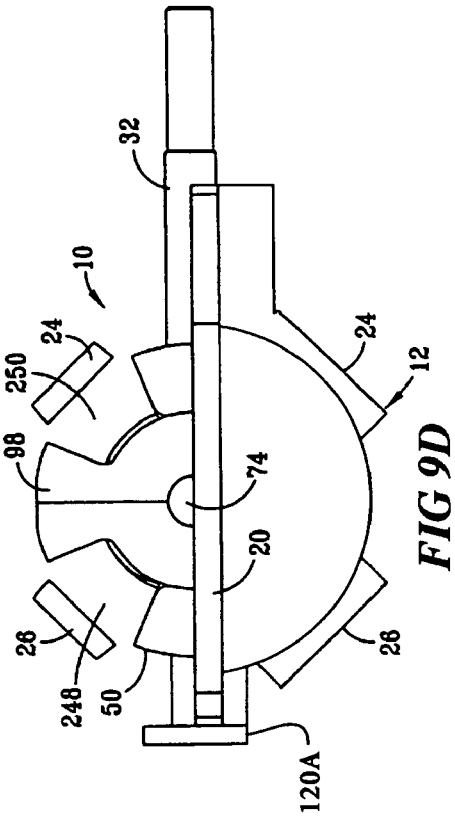
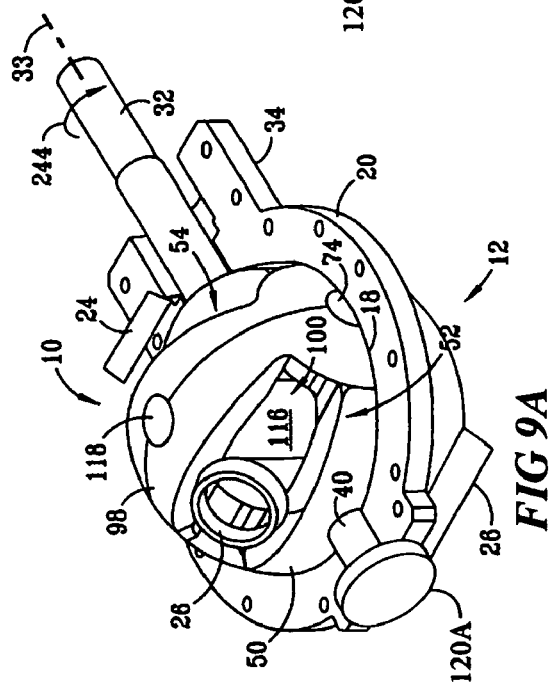
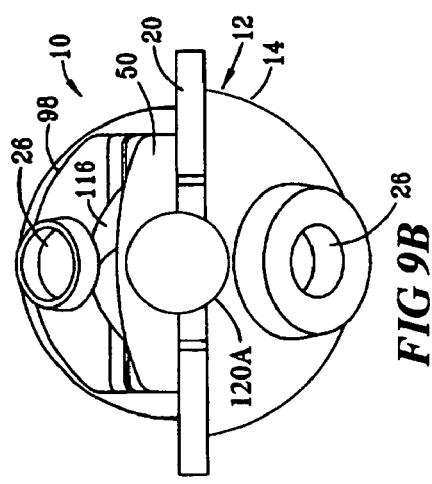
FIG 9C
FIG 9D
FIG 9A
FIG 9B

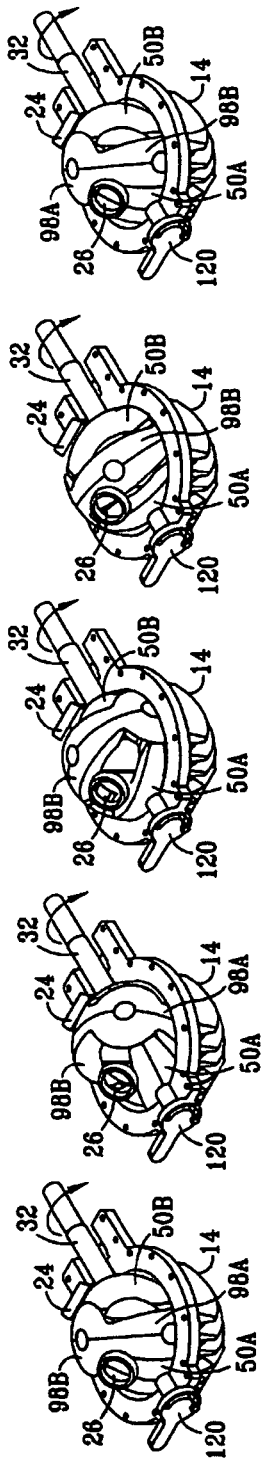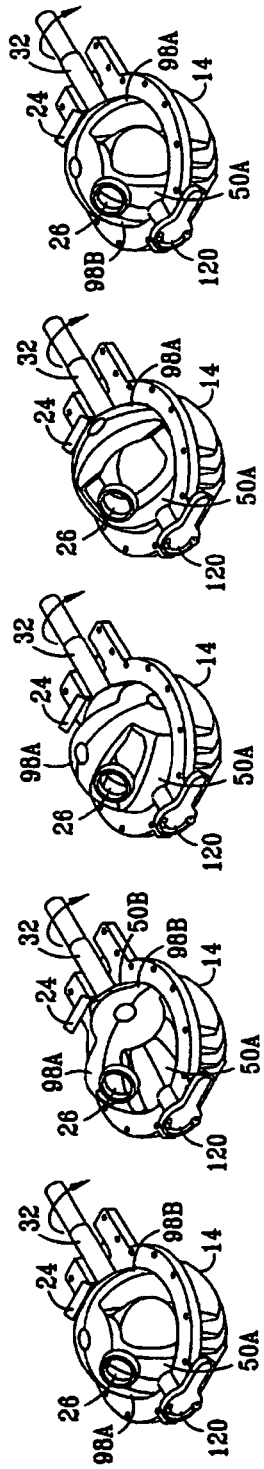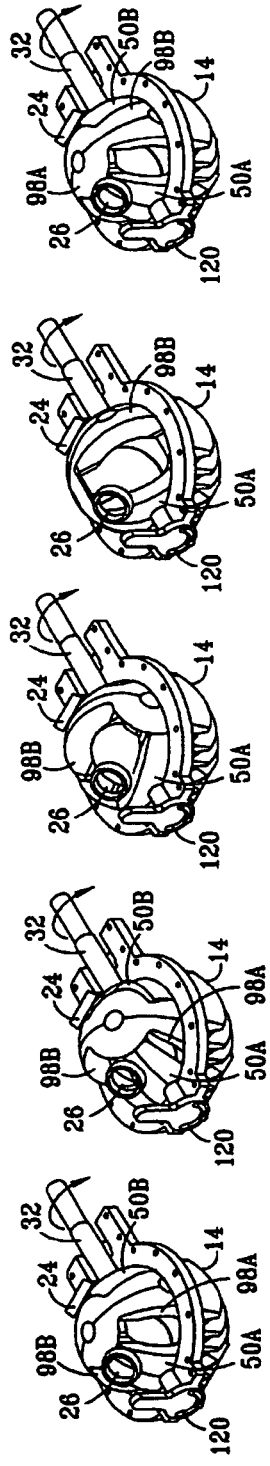

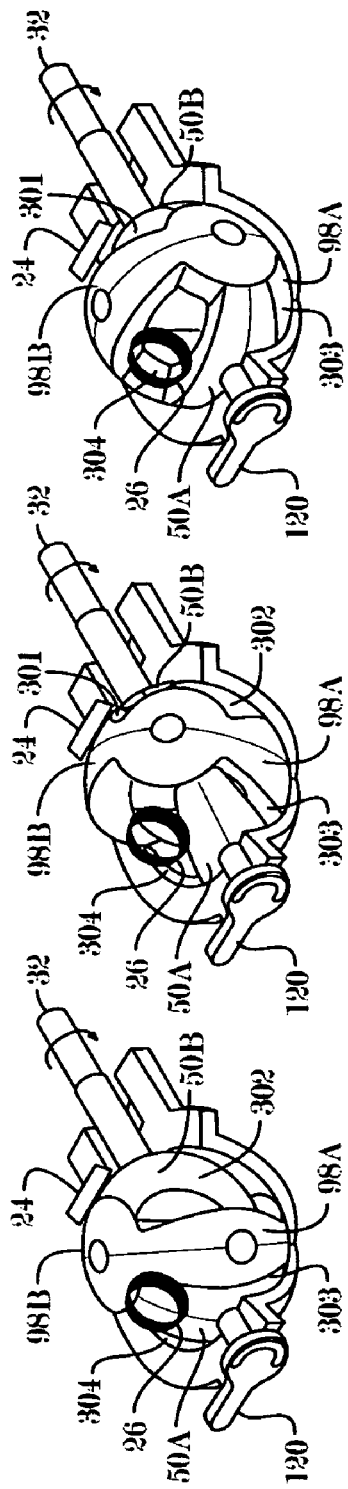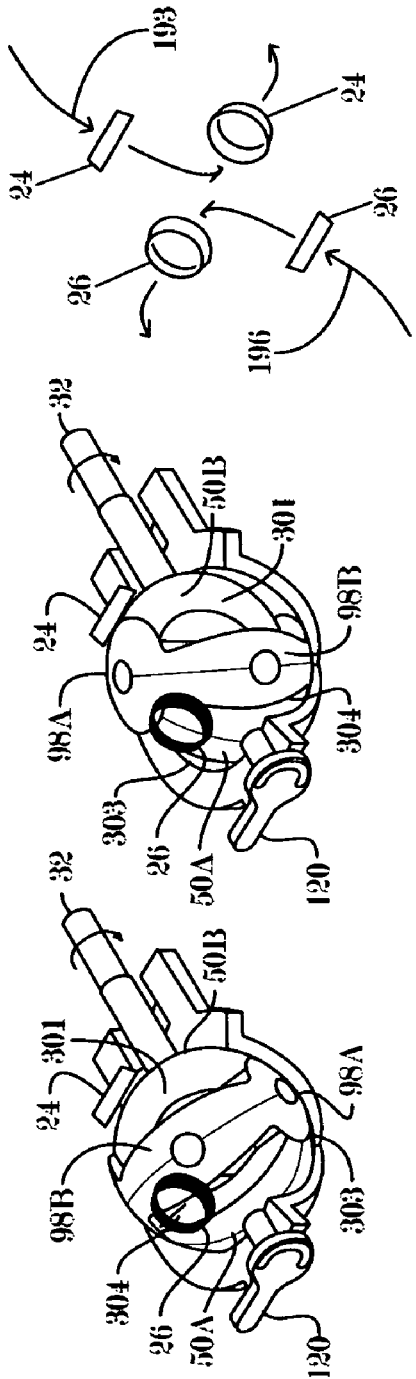
FIG 20A  FIG 20B  FIG 20C
FIG 20D  FIG 20E  FIG 20F

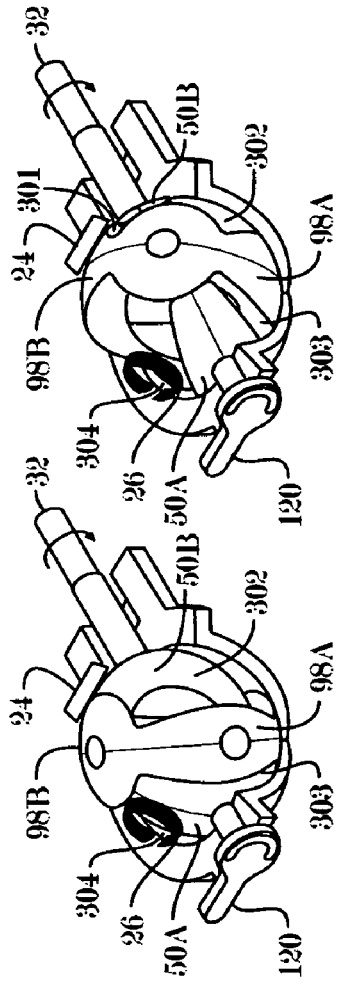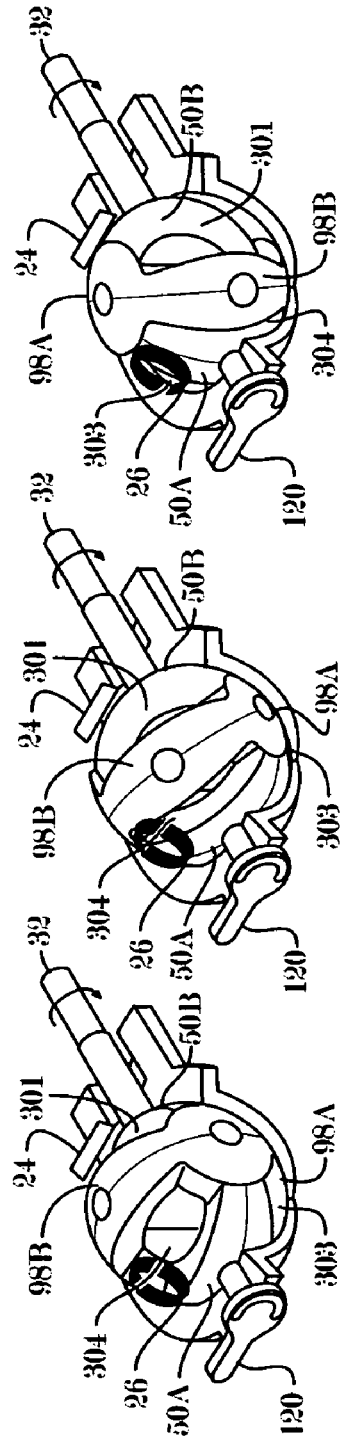

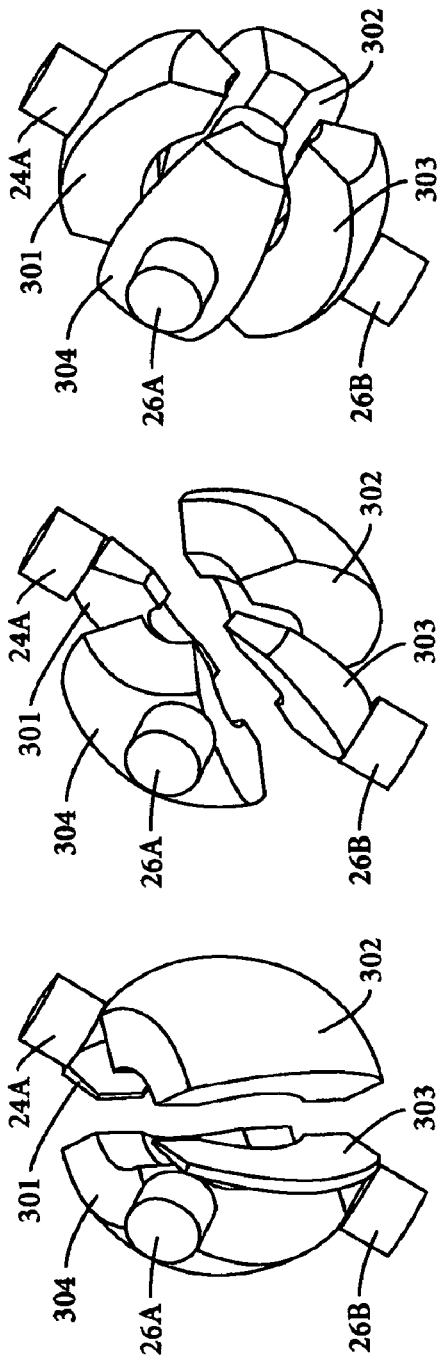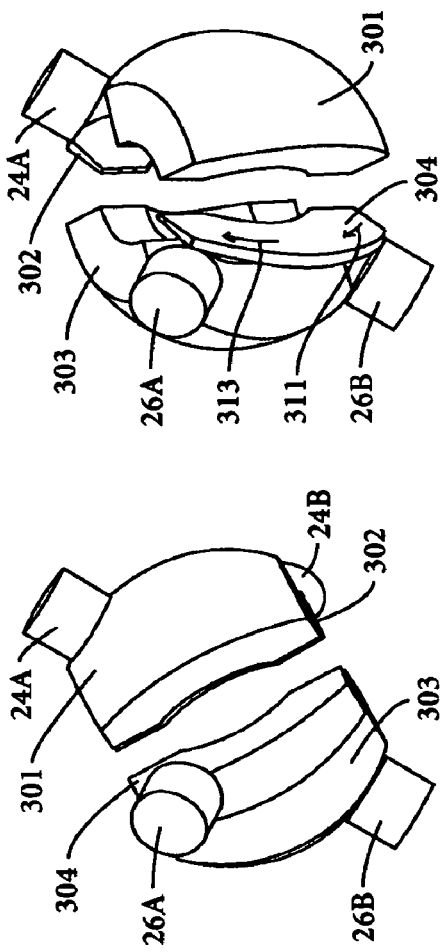

PULSATILE BLOOD PUMPING SYSTEMS

CROSS REFERENCE TO RELATED APPLICATIONS

This application is a continuation of Ser. No. 10/824,821 and claims priority of U.S. Pat. No. 7,014,605 filed Apr. 15, 2004.

TECHNICAL FIELD

The invention relates generally to artificial heart pumping systems that can be used either externally (non-implantable) or internally (implantable) with respect to the human body for maintaining life-sustaining circulation.

BACKGROUND

The failure of the heart to provide adequate circulation of blood is a serious life-threatening problem. Heart transplants have treated the most serious cases of heart failures. A heart transplants though is a drastic procedure with high risk and the supply of donors is limited when compared to the total need. Considerable research and development has been done therefore into developing artificial hearts that can replace the human heart. Currently most artificial heart blood pumping systems are used more as temporary heart assistants pending the location of a heart donor.

A variety of functional designs for artificial hearts are in the patent prior art and a number of functional designs now exist and are in use at various heart centers around the world. The AbioCor implantable replaceable heart, provided by ABIOMED, Inc. is a self-contained implantable replacement heart. This pump weighs about two pounds and consists of artificial ventricles that contain corresponding valves and a motor driven hydraulic pumping system. The hydraulic pumping system uses pressure to move blood from the artificial right ventricle to the lungs or from the artificial left ventricle to the rest of the body. To create this pressure the pump motor rotates at 4000 to 8000 rpm. Another system, the ABIOMED BVS-5000 is an air driven dual chamber blood pump placed outside the body used primarily for temporary left, right, or biventricular support of patients with heart failure. The pump houses two polyurethane chambers, an atrial chamber that fills with blood through gravitational force and a ventricle chamber that pumps blood by air-driven power. Two trileaflet valves separate the chambers.

The Thoratec HeartMate implantable pneumatic left ventricular assist system is based on an air-driven titanium alloy pump that weighs about 570 grams and consists of a blood chamber, an air chamber, a drive line and inflow and outflow conduits. Each conduit is a titanium cage that contains a valve within a Dacron fabric graft. The pump is powered and controlled by an external portable console. The Thoratec HeartMate II is an implantable left ventricular assist system based on a continuous axial flow in-line pump. There are other artificial blood pumping systems under development and in use.

The existing solutions have provided utility and prolonged lives. There are still many issues to be addressed however. Many of the prior solutions provide continuous flow whereas a problem free pulsatile flow that provides a more physiologic flow of blood is needed. Pulsatile flow is sometimes provided by flexible-volume chambers (bladders, tubing, bellows) but these are susceptible to wear and prone to thrombosis. Thrombosis as related to medical devices is the formation of blood clots on, or inside of, a medical device, and can lead to serious consequences. Flexible-volume chambers that do not completely or nearly completely expel their contained fluid during each stroke can also be prone to thrombosis. Another issue is simply size. Pumping systems with multiple chambers and the accompanying drive mechanism are typically too large to fit in smaller adults or children. Partially related to size is energy efficiency, with these systems requiring too much energy to operate. In addition to size though, many designs are inherently energy inefficient because of mechanisms that require reversing motion (pistons, bladders) that expends additional energy. Another issue evident from the above discussion of some of the existing systems is the use of valves. Valves not only add to size and complexity (and therefore reliability) but also are prone to calcification, wearing out and to thrombosis. Some of the prior art systems and devices also have problems with hemolysis (breakdown of red blood cells) due to either mechanical forces or shear forces in the motion of the fluid. Finally there is a definite need for easier flow modification of blood pumping systems. Many of the existing systems require separate drive force or shunting to accomplish this. Additionally, none of the prior art devices are known to provide two streams with simultaneous discharge pulsation peaks or simultaneous intake strokes, which simultaneity is physiologically desirable.

The above needs can be addressed by applying modifications of new pumping technology to the special problems of blood pumping systems.

Spherical rotary pumping systems have been developed that consist of a spherical housing within which one or more vanes rotate. This is in contrast to those devices that utilize a reciprocating, linearly moving piston. In the case of the spherical rotary pumps the vanes are rotated by a shaft to cause the fluid to flow through the device.

U.S. Pat. No. 5,199,864 to Stecklein discloses a rotary fluid pump that employs vanes rotating within a spherical housing and includes an interior carrier ring that guides a particular motion of the vanes so that they open and close to draw in and either pump or compress fluids, thereby creating a type of pulsatile flow. This patent also describes an embodiment (the "second embodiment") that uses an exterior carrier ring to guide the reciprocal motion of the vanes. These devices are highly efficient, and are capable of displacing large quantities of fluid relative to their size, so that the use of a small pump is possible. The flow of fluid is typically controlled by the rate at which the rotary vanes are rotated. By increasing the speed, more fluid is pumped through the device, while decreasing the speed decreases the amount of fluid pumped.

U.S. Pat. No. 6,241,493 to Turner discloses a particularly useful improvement on this type of spherical fluid machine that is configured to enable adjustments in both fluid capacity and fluid direction without changing the speed or direction of rotation of the vanes in the device by adjusting the orientation of an interior carrier ring. That patent is incorporated by reference into this application.

Fluid machines such as that described in U.S. Pat. No. 6,241,493 and U.S. Pat. No. 5,199,864 are also already ported, meaning that the manner in which the chambers communicate with the inlet and discharge ports negates the need for valves. They can be especially long running from a maintenance perspective because there is no direct physical contact between either the vanes and the central sphere around which they rotate nor physical contact between the vanes and the exterior housing of the machine. Low leakage between chambers is achieved by maintaining small clearances that minimize slippage or fluid loss across the clearances.

Further improvements to these types of spherical rotary pumps are disclosed in U.S. patent application Ser. No.

10/784,709 by the inventor of the instant invention and that application is incorporated herein by reference in its entirety. These improvements included adding stability to the design, adding internal cooling, incorporating the ability to pump multiple fluids, and adding critical seals. Some of these improvements were aimed at the dual use of this type of a pump as a fluid pump as well as a compressor and/or motor in industrial applications. It is important to note that none of the prior art references on these spherical rotary pumps recognized their potential value as an artificial heart or as a ventricular assist device nor were the particular issues inherent in adapting this solution for those applications recognized or dealt with in these references. For example, issues related to biocompatibility, hemocompatibility, hemolysis and thrombosis were not addressed. The crux of the instant invention is the recognition of the need and the adaptation of these devices for this application.

SUMMARY

These and other needs are addressed by the present invention, which simultaneously provides a method and apparatus for providing a reliable, adjustable pulsatile blood flow with a very small, efficient spherical blood pump that can be used as an implantable or external device and that can be easily configured to pump either one or two fluids. The instant invention also includes a number of other embodiments that address the particular needs of blood pumping systems that will be connected to a living organism, including improved biocompatibility, improved hemocompatibility and significantly reduced hemolysis and thrombosis.

For purposes of the description here the solutions will be described with respect to a fluid machine similar to the one described in U.S. Pat. No. 6,241,493. Accordingly that prior art fluid machine will be described first in some detail. It should be recognized however that the instant invention could be potentially applied in any spherical pump such as those described in U.S. Pat. No. 5,199,864 or in U.S. Pat. No. 5,147,193.

One aspect of the pulsatile blood pumping system of this invention then includes at least a housing having a wall defining a generally spherical interior, the housing having at least one intake port opening in communication with the interior of the housing and at least one discharge port opening in communication with the interior of the housing, and further including at least a first shaft mounted for rotation relative to the housing about a primary axis, where at least a portion of the first shaft extends through the housing wall and where at least one primary vane is disposed within the interior of the housing that rotates about the primary axis of the first shaft; at least one secondary vane disposed within the interior of the housing and mounted to the primary vane on a first pivotal axis, the secondary vane pivotally oscillating between alternating relatively open and closed positions with respect to the primary vane and defining at least a chamber within the housing interior having a volume which varies as the primary vane is rotated about the primary axis; and where the at least one intake port opening and at least one discharge port opening are connected to circulate at least one blood fluid through a living organism.

The pulsatile blood pumping system of this invention also includes at least a housing having a wall defining a generally spherical interior, the housing having at least one port opening in communication with the interior of the housing; a first shaft mounted for rotation relative to the housing about a primary axis, wherein at least a portion of the first shaft extends through the housing wall; at least one primary vane disposed within the interior of the housing that rotates about the primary axis of the first shaft; at least one secondary vane disposed within the interior of the housing and mounted to the primary vane on a first pivotal axis, the secondary vane pivotally oscillating between alternating relatively open and closed positions with respect to the primary vane and defining at least a chamber within the housing interior having a volume which varies as the primary vane is rotated about the primary axis; the secondary vane being pivotally coupled to a carrier ring, so that the secondary vane is pivotal about a second pivotal axis perpendicular to the axis of rotation of the carrier ring causing the secondary vane to reciprocate between relatively open and closed positions as the secondary vane is rotated about the primary axis by the first shaft; the axis of rotation of the carrier ring being oriented at an oblique angle in relation to the primary axis of the first shaft; a second shaft that extends into the interior of the housing opposite the first shaft, the second shaft having a spherical portion about which the primary vane rotates and wherein the carrier ring is rotatably carried on the spherical portion of the second shaft; and wherein the at least one intake port opening and at least one discharge port opening are connected to circulate at least one blood fluid through a living organism.

The pulsatile blood pumping system of this invention also includes a housing having a wall defining a generally spherical interior, the housing having at least one intake port opening in communication with the interior of the housing and at least one discharge port opening in communication with the interior of the housing, and including at least a first shaft mounted for rotation relative to the housing about a primary axis, wherein at least a portion of the first shaft extends through the housing wall; at least one primary vane disposed within the interior of the housing that rotates about the primary axis of the first shaft; at least one secondary vane disposed within the interior of the housing and mounted to the primary vane on a first pivotal axis, the secondary vane pivotally oscillating between alternating relatively open and closed positions with respect to the primary vane and defining at least a chamber within the housing interior having a volume which varies as the primary vane is rotated about the primary axis; wherein the at least one intake port opening and the at least one discharge port opening are operated simultaneously to both input and discharge blood fluids.

Another aspect of the instant invention is a method for simultaneously inputting and discharging at least one blood fluid through a blood pumping system in a pulsatile manner comprising the steps of providing a housing having a wall defining a generally spherical interior, the housing having at least one intake port opening in communication with the interior of the housing and at least one discharge port opening in communication with the interior of the housing through which at least one blood fluid flows connecting at least one intake port opening and at least one discharge port opening to enable the circulation of at least one blood fluid through the living organism, rotating a first shaft mounted for rotation relative to the housing about a primary axis, wherein at least a portion of the first shaft extends through the housing wall; rotating at least one primary vane disposed within the interior of the housing that rotates about the primary axis; providing at least one secondary vane disposed within the interior of the housing and mounted to the primary vane on a first pivotal axis; and rotating the primary vane about the primary axis with the secondary vane pivotally oscillating between alternating relatively open and closed positions with respect to the primary vane; the housing, the primary vane, and the secondary vane defining at least one fluid chamber for containing fluid within the housing interior having a volume that varies as the primary vane is rotated about the primary axis.

Another aspect of the instant invention is a method for circulating at least one blood fluid through a living organism in a pulsatile manner comprising the steps of: providing a housing having a wall defining a generally spherical interior, the housing having at least one intake port opening in communication with the interior of the housing and at least one discharge port opening in communication with the interior of the housing through which at least one blood fluid flows connecting at least one intake port opening and at least one discharge port opening to enable the circulation of at least one blood fluid through the living organism, rotating a first shaft mounted for rotation relative to the housing about a primary axis, wherein at least a portion of the first shaft extends through the housing wall; rotating at least one primary vane disposed within the interior of the housing that rotates about the primary axis; providing at least one secondary vane disposed within the interior of the housing and mounted to the primary vane on a first pivotal axis; and rotating the primary vane about the primary axis with the secondary vane pivotally oscillating between alternating relatively open and closed positions with respect to the primary vane; the housing, the primary vane, and the secondary vane defining at least one fluid chamber for containing fluid within the housing interior having a volume that varies as the primary vane is rotated about the primary axis.

The instant invention also includes a method for simultaneously flowing a first fluid and a second fluid through the same pulsatile blood pumping system including at least the steps of: providing a housing having a wall defining a generally spherical interior, the housing having at least one port opening in communication with the interior of the housing through which fluid from a fluid source is allowed to flow; providing a first shaft mounted for rotation relative to the housing about a primary axis, wherein at least a portion of the first shaft extends through the housing wall; providing at least one primary vane disposed within the interior of the housing that rotates about the primary axis; providing at least one secondary vane disposed within the interior of the housing and mounted to the primary vane on a first pivotal axis; rotating the primary vane about the primary axis with the secondary vane pivotally oscillating between alternating relatively open and closed positions with respect to the primary vane, the housing, the primary vane, and the secondary vane defining a fluid chamber for containing fluid within the housing interior having a volume that varies as the primary vane is rotated about the primary axis; and providing a first fluid and a second fluid and connecting the first and second fluids to appropriate port openings to enable separate movement of the first and second fluids through the pulsatile blood pumping system.

BRIEF DESCRIPTION OF THE DRAWINGS

For a more complete understanding of the present invention, and the advantages thereof, reference is now made to the following descriptions taken in conjunction with the accompanying drawings, in which:

FIG. 5 is an exploded perspective view of a fixed second shaft assembly of the pump of FIG. 1;

FIG. 6 is a perspective view of a flow capacity control lever for rotating the second shaft of FIG. 5;

FIG. 7 is a cross-sectional view of the lever of FIG. 6 taken along the lines 7-7;

FIG. 9A is a perspective view of the pump of FIG. 1 shown with the upper half of the housing removed;

FIG. 9B is a front elevational view of the pump of FIG. 9A;

FIG. 9C is a top plan view of the pump of FIG. 9A;

FIG. 9D is a side elevational view of the pump of FIG. 9A;

FIGS. 10A-10E are sequenced perspective views of the pump of FIGS. 9A-9D with the control lever in the 0 degree position, as the input shaft of the pump is rotated 180 degree during the pump's operation;

FIGS. 12A-12E are sequenced perspective views of the pump of FIGS. 11A-11D, with the control lever in the 180 degree position, as the input shaft of the pump is rotated 180 degrees during the pump's operation;

FIGS. 14A-14E are sequenced perspective views of the pump of FIGS. 13A-13D, with the control lever in the 90 degree or neutral position, as the input shaft of the pump is rotated 180 degrees during the pump's operation.

FIGS. 20A-20E are sequenced perspective views of the pump of FIGS. 9A-9D with the control lever in the 0 degree position, as the input shaft of the pump is rotated 180 degree during the pump's operation, showing the simultaneous flow of two fluids through the pump.

FIG. 20F is a view of the port openings only of FIG. 20A-20E to show the flow of two different fluids.

FIGS. 23A-23E are sequenced perspective views of the pump of FIGS. 9A-9D with the control lever in the 0 degree position, as the input shaft of the pump is rotated 180 degree during the pump's operation, showing the simultaneous flow of two fluid streams at two different flow rates through the pump.

FIGS. 26A-26E are sequenced perspective views of the pump of FIGS. 9A-9D with the control lever in the 0 degree position, as the input shaft of the pump is rotated 180 degree during the pump's operation, showing only the volumes occupied by the fluid in the fluid chambers and fluid ports.

DETAILED DESCRIPTION

Figure 1:
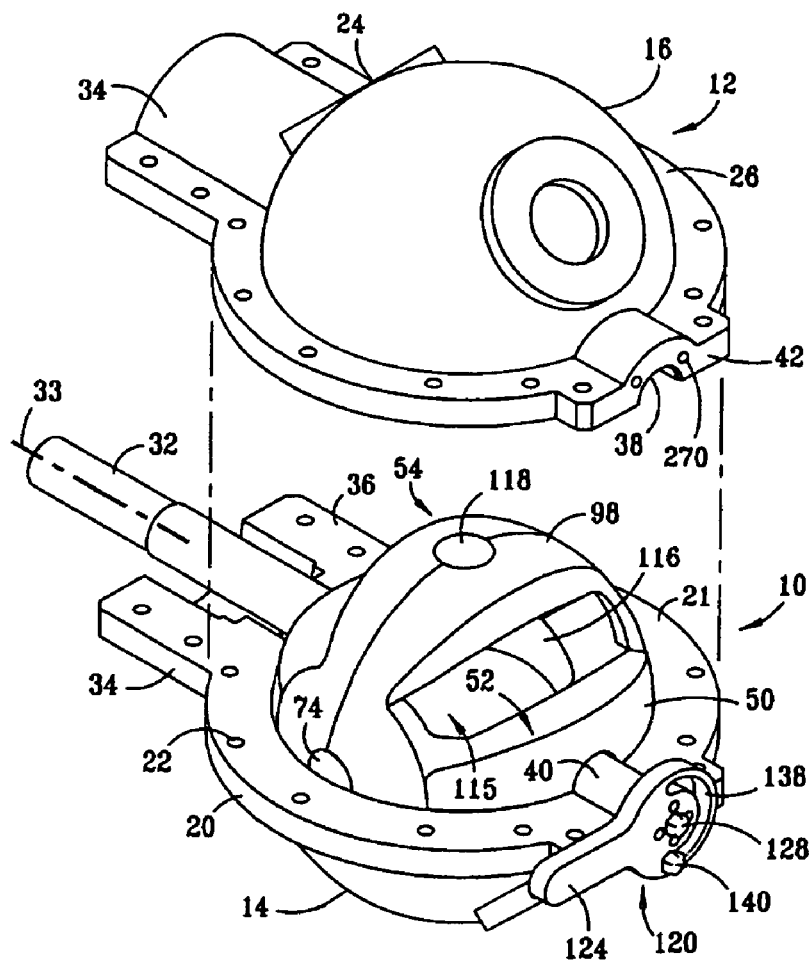
FIG. 1 is a front perspective view of a pulsatile blood pump, shown with the upper half of a housing of the pump exploded away to reveal internal components of the device.

Referring to FIG. 1 of the drawings, the reference numeral 10 generally designates a pulsatile blood pumping system of the type that can apply the improvements of the instant invention. The pump 10 is generally similar in construction to the device described in U.S. Pat. No. 6,241,493.

Figure 2:
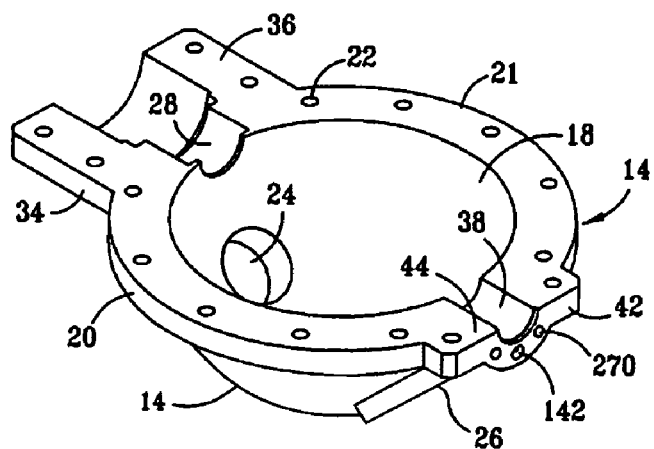
FIG. 2 is a perspective view of the lower half of the housing of the pump of FIG. 1 with the internal components removed.

The pump 10 includes a housing 12, which is formed into two halves 14, 16. Each half 14, 16 of the housing 12 is generally configured the same as the other and has a hemispherical interior cavity 18 (FIG. 2), which forms a spherical interior of the housing 12 when the two halves 14, 16 are joined together. Each housing half or piece 14, 16 is provided with a circular flange 20 having a flat facing surface 21 which extends around the perimeter of the cavity 18 and which abuts against and engages the corresponding flange 20 of the other housing piece 14, 16. The flange face 21 lies in a plane that generally divides the spherical housing interior 18 into two equal hemispherical halves when the housing halves 14, 16 are joined together.

A fluid tight seal is formed between the housing halves 14, 16 when the halves 14, 16 are joined together. Formed in each housing piece 14, 16 are rear and front fluid ports 24, 26 that communicate between the exterior of the housing and the housing interior 18. The fluid ports 24, 26 are circumferentially spaced apart approximately 90 degrees from the next adjacent port, with the approximate center of each fluid port being contained in a plane oriented perpendicular to the flange faces 21 and that bisects the interior of the housing 12 when the housing halves 14, 16 are joined together. The ports 24, 26 are positioned about 45 degrees from the flange faces 21 on each housing half 14, 16.

Formed at the rearward end of each housing half 14, 16 adjacent to the rearward port 24 is a recessed area 28 formed in the circular flange 20 for receiving a main input shaft 32 (FIG. 1), which extends for a distance into the housing interior 18. This shaft will be referred to as either the first or the input shaft. The primary axis or axis of rotation 33 of the input shaft 32 lies generally in the same plane as the flange faces 21. An input shaft collar 34 extends outwardly from the housing halves 14, 16 and is provided with a similarly flanged surface 36 for facilitating joining the housing halves together.

Located at the forward end of the housing 12 opposite the collar 34 in each housing half 14, 16 is a recessed area 38 formed in the circular flange 20 to form a shaftway for receiving a second shaft 40 (FIG. 1). A neckpiece 42 extends outwardly from the circular flange 20 and is also provided with a flanged surface 44 to facilitate joining of the housing halves together.

Figure 3:
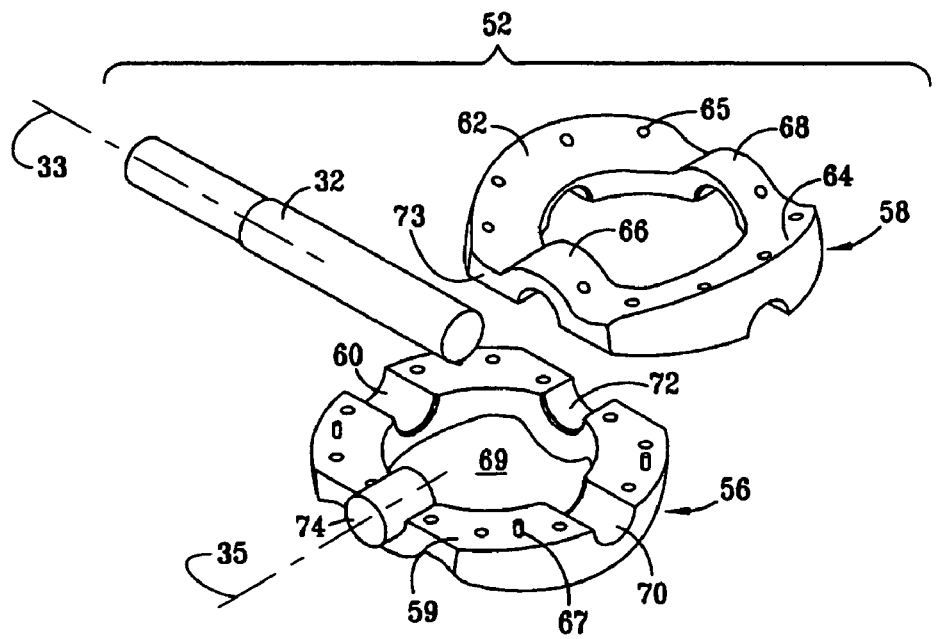
FIG. 3 is a perspective view of a input shaft and primary vane assembly of the pump of FIG. 1, shown with the primary vane assembly exploded into two halves.

The housing 12 houses primary and secondary vane assemblies 52, 54, respectively. Referring to FIG. 3, the primary vane assembly, designated generally at 52, is formed into two halves 56, 58. The primary vane halves 56, 58 are generally configured the same, each having a generally flat inner surface 59 that abuts against the inner surface of the other half. The primary vane halves 56, 58 each have opposite vane members 62, 64, that are joined together at opposite ends by integral hinge portions 66, 68 to define a central circular opening 69. When the primary vane halves 56, 58 are joined together, the vane members 62 and 64 form a single opposing vane.

The vane members 62 are each provided with an input shaft recess 60 formed in the flat surface 59 for receiving and coupling to the input shaft 32 when the vane halves 56, 58 are joined together. The primary vane assembly 52 is rigidly coupled to the input shaft 32 so that rotation of the input shaft 32 is imparted to the primary vane assembly 52 to rotate the combined vanes 56, 58 within the housing interior 18.

Similarly, the vane members 64 are provided with a second shaft recess 70 formed in the flat surface 59 for receiving the second shaft 40. The second shaft recess 70 is configured to allow the primary vane assembly 52 to freely rotate about the second shaft 40. The outer ends of the vane members 62, 64 have a generally convex spherical lune surface configuration corresponding to the spherical interior 18 of the housing 12.

The hinge portions 66, 68 are each provided with a stub shaft recess 72. A stub shaft 74 is shown provided with the hinge portion 66 of the vane half 56. This stub shaft 74 may be integrally formed with one of the vane halves 56, 58 or may be a separate member that is fixed in place. As is shown, the stub shaft 74 projects a distance outward beyond the hinge portion 66. The hinge portions 66, 68 are each squared or flat along the outer side edges 73.

Figure 4:
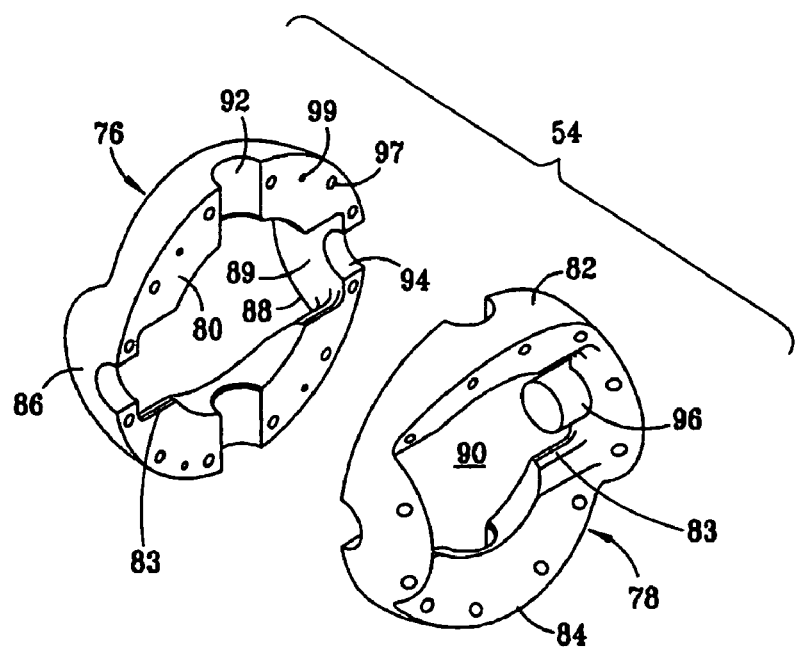
FIG. 4 is a perspective view of a secondary vane assembly of the pump of FIG. 1, shown with the secondary vane assembly exploded into two halves.

Referring to FIG. 4, the secondary vane assembly 54 is also shown being formed in two halves 76, 78, each half 76, 78 being generally similar in construction. The secondary vane halves 76, 78 are generally configured the same, each having an inner surface 80, which is generally flat and which abuts against the inner surface of the other vane half. The secondary vane halves 76, 78 each have opposite vane members 82, 84, that are joined together at opposite ends by integral hinge portions 86, 88 to define a central circular opening 90. When the secondary vane halves 76, 78 are joined together; the vane members 82 and 84 form a single opposing vane.

The vane members 82, 84 are each provided with pivot post recesses 92 formed in the inner surfaces 80 of each vane half 76, 78. The outermost ends of the vane members 82, 84 also have a generally convex spherical lune surface configuration corresponding to the spherical interior 18 of the housing 12.

The hinge portions 86, 88 are each provided with a stub shaft recess 94. A second stub shaft 96 is shown provided with the hinge portion 88 of the vane half 78. This stub shaft 96 may be integrally formed with one of the vane halves 76, 78 or may be a separate member that is fixed in place. As is shown, the stub shaft 96 projects a distance inward from the hinge portion 88. Both the hinge portions 86, 88 are squared or flat along the inner side edges 89 to correspond to the flat outer side edges 73 of the hinge portions 66, 68 of the primary vane halves 56, 58. The shapes of narrow ridges 83 generally complement the shape of the exterior surfaces of hinge portions 66, 68. The exterior of the hinge portions 86, 88 are in the form of a convex spherical segment or sector that is contoured smoothly with the curved surface of the outer ends of the vane members 82, 84, and corresponds in shape to the spherical interior 18 of the housing 12.

When the primary and secondary vanes 52, 54 are coupled together (FIG. 3) and mounted to the main input shaft 32, the stub shafts 74, 96 are generally concentric. The stub shaft 74 of the primary vane assembly 52 is received within the recesses 94 of the hinge portion 86 of the secondary vane assembly 54 to allow relative rotation of the secondary vane assembly 54 about the stub shaft 74. Likewise, the stub shaft 96 of the secondary vane assembly 54 is received within the recesses 72 of the hinge portion 68 of the primary vane assembly 52 and allows relative rotation of the primary vane assembly 52 about the stub shaft 96. In this way, the primary and secondary vanes assemblies 52, 54 remain interlocked together while the secondary vane assembly 54 is allowed to pivot relative to the primary vane assembly 52 about a first pivotal axis 35 that is perpendicular to the primary axis 33 of the input shaft 32.

FIG. 5 shows an exploded view of a fixed second shaft or race assembly 100. The second shaft assembly 100 is comprised of the cylindrical second shaft 40, which is received in the recesses 38 of the housing halves 14, 16, as discussed previously. The cylindrical second shaft 40 is coaxial with the primary axis 33 of the input shaft 32 when mounted to the housing 12. At the inner end of the shaft 40 is a spherical shaft portion 102 in the form of a sphere section. Projecting from the inner side of the spherical shaft portion 102 is a cylindrical carrier ring shaft 104. The longitudinal axis of the carrier ring shaft 104 is oriented at an oblique angle with respect to the axis of shaft 40. This angle may vary, but is preferably between about 30 degrees to 60 degrees, with 45 degrees being the preferred angle. A boss 106 projects from the end of the shaft 104 to facilitate mounting of an end cap 108, which is in the form of a spherical section. The end cap 108 is provided with a recess 110 for receiving the boss 106 of shaft 104. In the embodiment shown, a pair of threaded fasteners 112, such as screws or bolts, which are received within eccentrically disposed threaded bolt holes 114 formed in the boss 106, are used to secure and fix the end cap 108 to the shaft 104. Two or more fasteners may be used. Because the fasteners are eccentrically located with respect to the axis of the shaft 40, they prevent relative rotation of the end cap 108 with respect to the shaft 40.

The end cap 108 is used to secure a central carrier ring 116, which is rotatably mounted on the carrier ring shaft 104. The carrier ring 116 is configured with an outer surface in the form of a spherical segment so that when the carrier ring 116 is mounted on the shaft 104 and the end cap 108 is secured in place, the combination of the spherical portion 102, carrier ring 116 and end cap 108 generally form a complete sphere that is joined to the end of the shaft 40. This complete sphere is designated generally as central ball 115. The diameter of this sphere generally corresponds to the diameter of the central openings 69, 90 of the primary and secondary vane assemblies 52, 54, respectively, to allow the vane assemblies 52, 54 to rotate about this spherical portion of the second shaft assembly 100, while being in close engagement thereto. The carrier ring 116 is approximately centered between the spherical portion 102 and the end cap 108.

The carrier ring 116 is provided with oppositely projecting pivot posts 118 that project radially outward from the outer surface of the carrier ring 116. The posts 118 are concentrically oriented along an axis that is perpendicular to the axis of rotation of the carrier ring 116. The posts 118 are received within the pivot post recesses 92 of the secondary vane halves 76, 78 when the vane assembly 50 is mounted over the spherical portion of the second shaft assembly 100 formed by the spherical portion 102, carrier ring 116 and end cap 108.

Coupled to the second shaft 40 opposite the spherical portion 102 is a flow capacity control lever 120 for manually rotating the shaft 40 and spherical portion 102. The control lever 120, shown in more detail in FIGS. 6 and 7, has a generally circular-shaped body portion 122. A lever arm 124 extends from the body portion 122. Formed generally in the center of the body portion 122 is a bolt hole 126 for receiving a bolt 128 for fastening the lever 120 to the shaft 40 by means of a central, threaded bolt hole 130 formed in the outer end of the shaft 40. Spaced around bolt hole 126 are dowel holes 132 which correspond to dowel holes 134 formed in the shaft. Dowels 136 are received within the dowel holes 132, 134 to prevent relative rotation of the control lever 120 with respect to the shaft 40. Although one particular method of coupling the lever 120 to the shaft 40 is shown, it should be apparent to those skilled in the art that other means may be used as well. Control lever 120 can have smaller profiles as shown by control lever 120A shown later in FIGS. 9, 11, and 13. The control lever acts as an adjustable vane guide bearing member to oscillate the secondary vane to various opening positions relative to the primary vane.

An arcuate slot 138 that extends in an arc of about 180 degrees is formed in the body portion 122 of the lever 120 for receiving a setscrew or bolt 140. The arcuate slot 138 overlays a threaded bolt hole 142 formed in the housing neck piece 42 of the housing half 14, when the shaft assembly 100 is mounted to the housing 12. The setscrew 140 is used to fix the position of the lever 120 to prevent rotation of the shaft 40 once it is in the desired position. By loosening the setscrew 140, the lever 120 can be rotated to various positions to rotate the shaft assembly 100, with the setscrew 140 sliding within the slot 138.

Figure 8A:
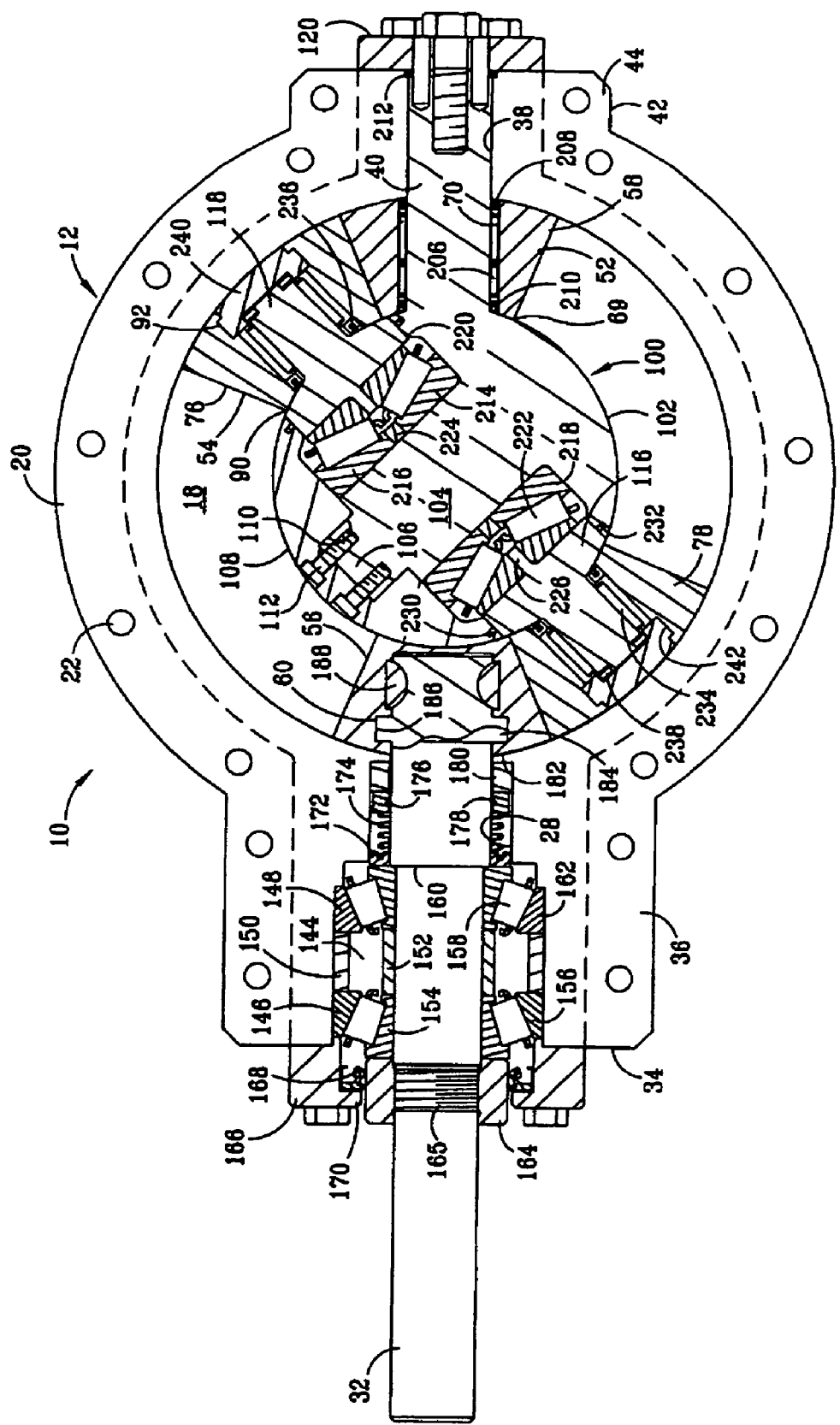
FIG. 8A is a detailed cross-sectional view of the pump of FIG. 1.

FIG. 8A is a longitudinal cross-sectional view of the assembled pump 10 shown in more mechanical detail. Although one particular embodiment is shown, it should be apparent to those skilled in the art that a variety of different configurations and components, such as bearings, seals, fasteners, etc., could be used to ensure the proper operation of the pump 10. The embodiment described is for ease of understanding the invention and should in no way be construed to limit the invention to the particular embodiment shown.

As can be seen, the input shaft 32 extends through the collar 34 at the rearward end of the housing 12. The collar 34 defines a cavity 144 that houses a pair of longitudinally spaced input shaft roller bearing assemblies 146, 148. Each of the roller bearing assemblies 146, 148 is comprised of an inner race 154 and an outer race 156, which houses a plurality of circumferentially spaced tapered roller bearings 158 positioned therebetween. Spacers 150, 152 maintain the roller bearing assemblies 146, 148 in longitudinally spaced apart relationship along the input shaft 32, with the inner race 154 of the roller bearing assembly 148 abutting against an outwardly projecting annular step 160 of the drive shaft 32, and the outer race 156 abutting against a inwardly projecting annular shoulder 162 of the collar 34.

A bearing nut 164 threaded onto a threaded portion 165 of the input shaft 32 abuts against the inner race 154 of bearing assembly 146 and preloads the inner races 154. Bolted to the end of the collar 34 is a bearing retainer ring 166. The bearing retainer ring 166 abuts against the outer race 156 of bearing assembly 146 and preloads the outer bearing races 156. The retainer ring 166 also serves to close off the cavity 144 of the housing collar 34. An annular seal 168 seated on the annular lip 170 of the retainer ring 166 bears against the exterior of the bearing nut 164 to prevent leakage of lubricant from the bearing cavity 144.

Located within the recessed area 28 and surrounding the input shaft 32 is a washer 172 that abuts against the inner race 154 of the bearing assembly 148. A compressed coiled spring 174 abuts against the washer 172 and bears against a carbon sleeve 176. The sleeve 176 is provided with an O-ring seal 178 located within an inner annular groove of the sleeve 176. The sleeve 176 abuts against a fixed annular ceramic plate 180, which seats against an annular lip 182 projecting into the recessed area 28. The low coefficient of friction between the interfacing carbon sleeve 176 and ceramic plate 180 allows the sleeve 176 to rotate with the input shaft 32, while providing a fluid-tight seal to prevent fluid flow between the pump interior 18 and the collar cavity 144.

The input shaft 32 extends into the interior 18 of the housing 12 a short distance and is coupled to the primary vane assembly 52 within the recesses 60 formed in vane halves 56, 58. The end of the shaft 32 is provided with an annular collar 184 received in grooves 186 formed in the recesses 60 of the vane halves 56, 58 to prevent relative axial movement of the shaft 32 and vane assembly 52. Relative rotational movement between the vane assembly 52 and shaft 32 is prevented by key members 188 being received in key slots of the vane assembly 52 and shaft 32, respectively.

Surrounding the second shaft portion 40 within the recess 70 of the primary vane assembly 52 are longitudinal roller bearings 206. Seals 208, 210 are provided at either end of the roller bearing assembly 206 to prevent fluid from escaping along the second shaft 40 through recesses 70. A static O-ring seal 212 surrounds the shaft 40 at the interface of the lever arm 120 with housing neckpiece 42 to prevent fluid loss through shaftway 38.

Surrounding the carrier ring shaft 104 are roller bearing assemblies 214, 216. Each roller bearing assembly 214, 216 is comprised of an inner race 218 and an outer race 220 with a plurality of tapered roller bearings 222 therebetween. The inner races 218 of assemblies 214, 216 are spaced apart by means of a spacer 224. The inner face of the carrier ring 116 rests against the outer races 220. An annular web 226 projects radially inward from the inner annular face of the carrier ring 116 and serves as a spacer between the outer races 220 and prevents axial movement of the carrier ring 116 along the shaft 104. For spherical pump configurations that have the equivalent to carrier ring 116 on the outside of housing 12, the equivalent ring is preferably manufactured in two or more sections to allow ease of assembly of the pump. These sections may be, for example, two semicircular segments that divide the equivalent ring approximately across the diameter, or two circular segments that join at the center circumferential plane of the equivalent ring. The sections are then joined with fasteners.

Lip seals 230, 232 provided in inner faces of the end cap 108 and spherical portion 102, respectively, engage the side edges of the carrier ring 116 to prevent fluid from entering the annular space surrounding the carrier ring shaft 104 where the bearing assemblies 214, 216 are housed and which contains a suitable lubricant for lubricating the bearing assemblies 214, 216. At lower rates of rotation a lubricant or coolant may not be needed on a continual basis.

Axially oriented roller bearings 234 surround the pivot posts 118 to allow the secondary vanes 54 to rotate. Fluid seals 236 are provided at the base of posts 118. Radially oriented thrust bearings 238 located at the terminal ends of posts 118 and are held in place by thrust caps 240. The thrust caps 240 are held in place within annular grooves 242 formed in the pivot post recesses 92.

As can be seen, the outer ends of the primary vanes 52 and secondary vanes 54 are in close proximity or a near touching relationship to provide a clearance with the interior 18 of the housing 12. There is also a slight clearance between the spherical end portion of the fixed second shaft assembly 100 and the central openings 69, 90 of the primary and secondary vanes 52, 54. These clearances should be as small as possible to allow free movement of the vanes 52, 54 within the interior 18, while minimizing slippage or fluid loss across the clearances, and to allow for differences in thermal expansion between the housing 12, the vanes 52, 54 and the spherical portion 102 and end cap 108.

Figure 8B:
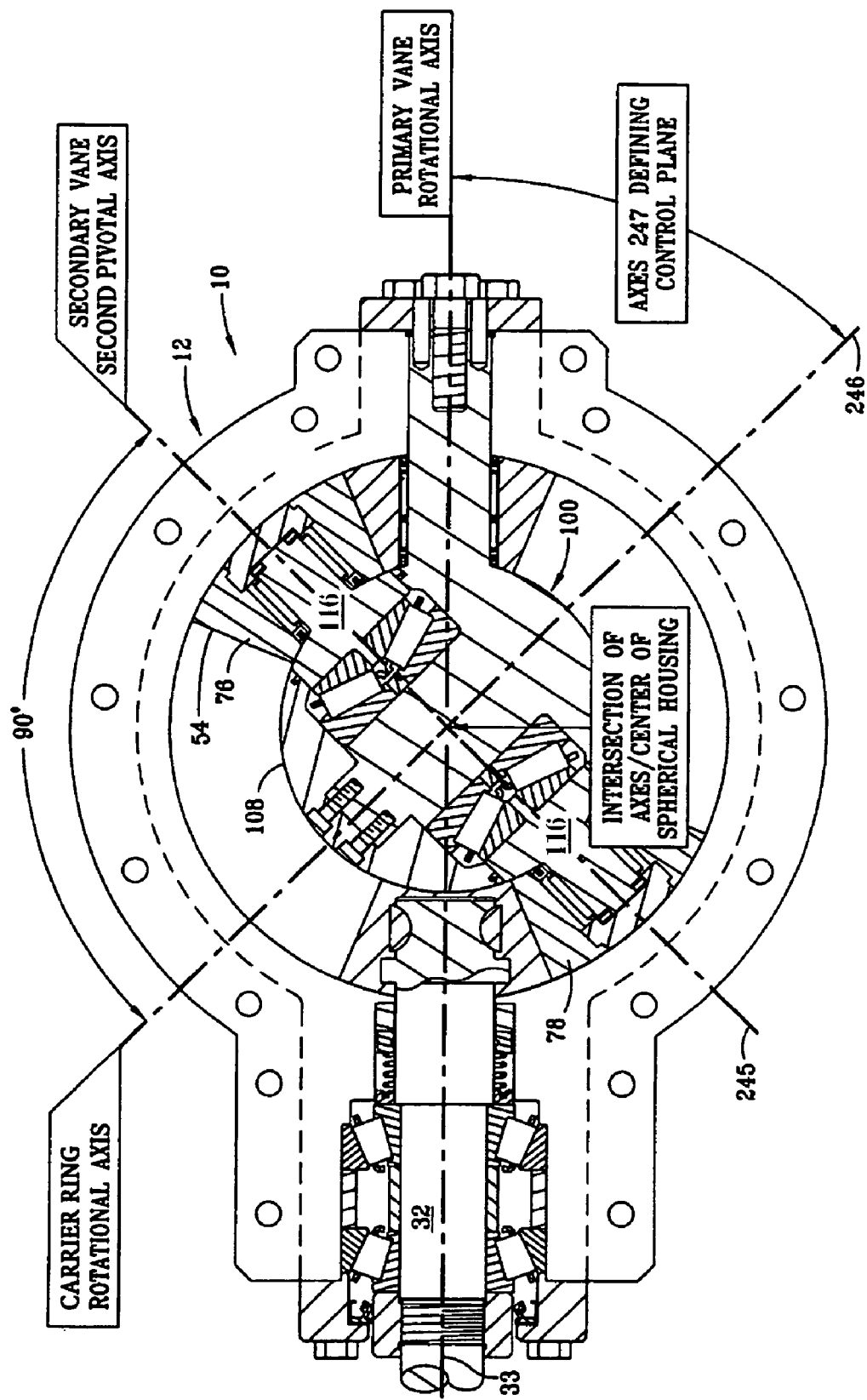
FIG. 8B is a cross-sectional view of the pump of FIG. 1, showing various rotational axes of the device.

FIG. 8B illustrates the relationship of the various rotational axes of the pump components. As shown, carrier ring 116 rotates about the carrier ring axis 246. The axis 246 intersects the primary vane axis 33 at an oblique angle and defines a control plane 247. The secondary vane 54 pivots about the pivot posts 118 about a secondary vane second pivotal axis 245 that remains perpendicular to the carrier ring axis 246. This second pivotal motion of the secondary vane is simultaneous with the pivotal motion of the secondary vane about the first pivotal axis perpendicular to the primary axis, which was discussed earlier.

Figure 8C:
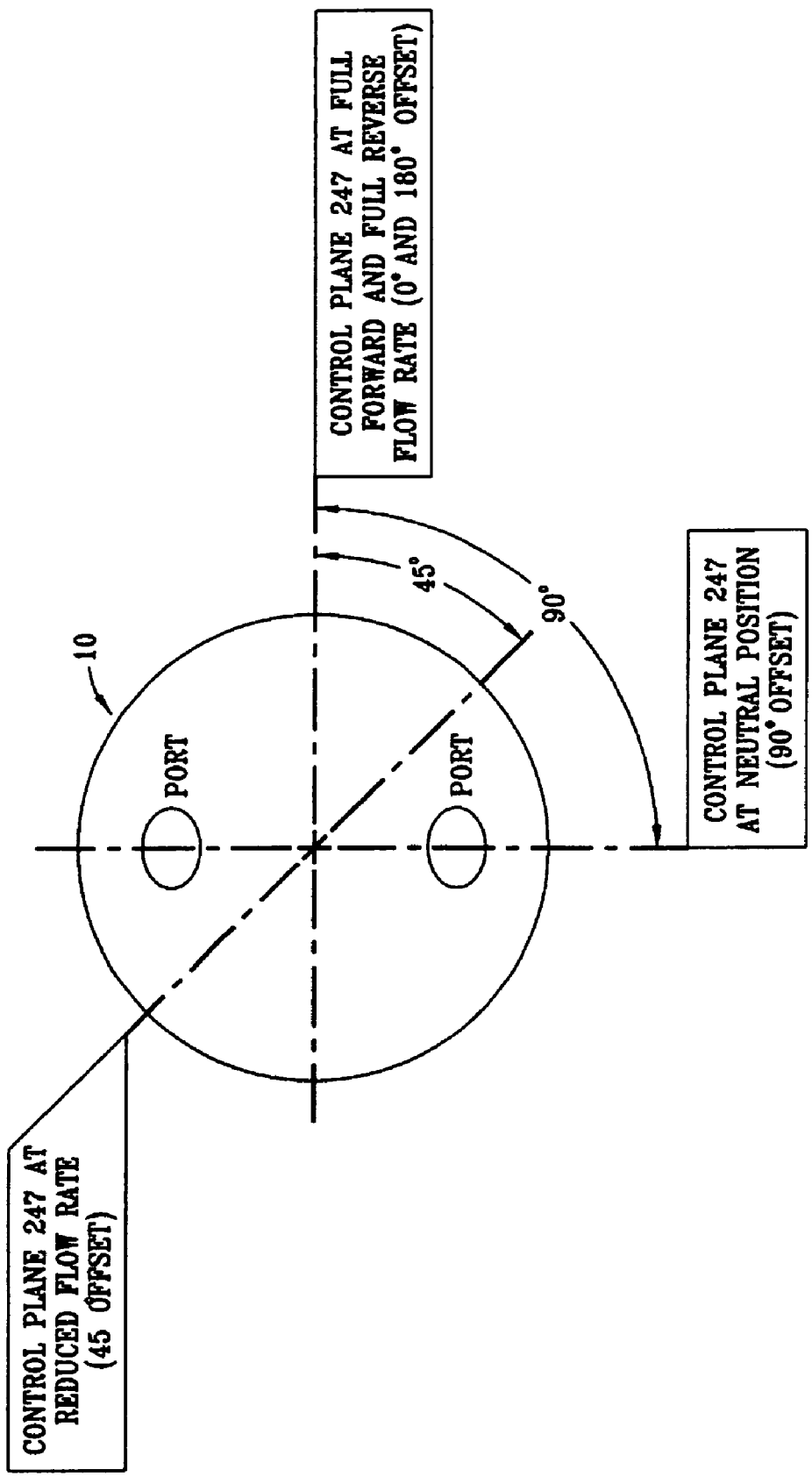
FIG. 8C is a schematical diagram of the pump housing showing the rotation of a control plane with respect to the pump housing.

FIG. 8C shows an end view of the pump 10 as viewed along the primary axis, and showing the various orientations of the timing or control plane 247 that may be achieved by rotating the second shaft assembly 100, as is described below.

Referring to FIGS. 9-14, the pump 10 is shown with the upper housing 16 removed to reveal the internal components of the pump 10. The ports 24, 26 of the upper housing 16, however, are shown to indicate their relative position if the upper housing 16 were present. Further, although the input shaft 32 may be rotated in either a clockwise or counterclockwise direction, for purposes of the following description the operation of the pump 10 is described wherein the input shaft 32 is rotated in a clockwise direction, as indicated by the arrow 244 in FIG. 9A.

Referring to FIGS. 9A-9D, the pump 10 is shown with control guide 120A rotated so that the carrier ring or secondary axis 246 is oriented at a 45 degree angle to the right of the primary axis 33, as viewed in FIG. 9C, so that the control plane 247 (FIGS. 8B and 8C) lies in a substantially horizontal plane that is generally the same or parallel to the plane of the flanges 20 which bisect the housing 12.

FIGS. 9A-9D show the primary and secondary vanes 50, 98 with the secondary vane 98 at a central intermediate position of its stroke. The forward port 26 of the upper housing 16 and the rearward port 24 of the lower housing 14 serve as discharge ports, while the rearward port 24 of the upper housing 16 and the forward port 26 of the lower housing 14 serve as intake ports. The primary and secondary vanes 50, 98 divide the spherical interior 18 of the housing into four chambers, as defined by the spaces between the primary and secondary vanes 50, 98 designated at 248, 250. Although not visible, corresponding spaces or chambers would be present in the lower housing half 14.

FIGS. 10A-10E show sequenced views of the pump 10 in operation with the control lever 120 in the 0 degree position as the input shaft 32 is rotated through 180 degrees of revolution. For ease in describing the operation, the opposing secondary vanes are labeled 98A, 98B, with the opposing primary vanes being designated 50A, 50B. As shown in FIGS. 9A and 9C, as the input shaft 32 is rotated, the primary and secondary vanes assemblies 52, 54 are rotated about the primary axis 33 within the housing interior 18. Because the secondary vane assembly 54 is pivotally mounted to the carrier ring 116 by means of pivot posts 118, the secondary vane assembly 54 causes the carrier ring 116 to rotate on the carrier ring shaft 104 (not shown) about the carrier ring axis 246. Because the carrier ring axis 246 is oriented at an oblique angle with respect to the primary axis 33, the carrier ring 116 causes each secondary vane 98A, 98B to reciprocate or move back and forth between a fully open position and a fully closed position.

FIG. 10A shows the pump 10 with the secondary vane 98A in the fully closed position with respect to primary vane 50A. In the fully closed position, the secondary vane 98A abuts against or is in close proximity to the primary vane 50A, so that the volume therebetween is minimal. In contrast, with respect to the opposing primary vane 50B, the vane 98A is in a fully open position so that the space between the vanes 98A and 50B is at its maximum. Any fluid within the space between vanes 98A, 50A is mostly fully discharged through the port 26 of the upper housing. There is a slight overlap or communication of the interfacing primary and secondary vanes 50A, 98A with the port 26 along its edge when in the fully closed position to accomplish this. In one aspect of the invention the primary vanes 50A, 50B are sized to completely cover and seal the ports 24, 26 so that slight rotation beyond this point causes the primary vanes 50A, 50B to close off communication with the chambers 248, 250 momentarily during rotation.

FIG. 10B illustrates the pump 10 with the shaft 32 rotated approximately 45 degrees from that of FIG. 10A. Here the secondary vane 98A begins to move to the open position with respect to the primary vane 50A. This draws fluid into the opening space through the lower inlet port 26 of the lower housing 14. The secondary vane 98B also begins to move to the closed position with respect to the primary vane 50A. Fluid located in the chamber between the primary vane 50A and secondary 98 is thus compressed or forced out of the upper discharge port 26 of the upper housing 16.

In a like manner, fluid located between the secondary vane 98A and primary vane 50B is discharged through the lower port 24 (not shown) of the lower housing 14, as the secondary vane 98A begins to move to the closed position with respect to the primary vane 50B. Fluid is also drawn through the inlet port 24 of the upper housing 16 as the secondary vane 98B is moved towards an open position with respect to the primary vane 50B.

FIGS. 10C and 10D show further rotation of the shaft 32 in approximately 45-degree increments. When the second shaft assembly 100 is in the 0 degree position, the timing is such that the chambers created by the primary and secondary vanes 50, 98 remain in continuous communication with ports 24, 26 during generally the entire stroke of the vane 50 between the closed and open positions. In this way fluid continues to be drawn into or discharged from the chambers as the secondary vanes 98 are moved to either the open or closed positions during rotation of the shaft 32.

FIG. 10E shows the pump 10 after the shaft 32 is rotated 180 degrees. The secondary vane 98B is in the fully closed position with respect to the primary vane 50A, just as the secondary vane 98A was when the shaft 32 was at the 0 degree position in FIG. 10A. By continuing to rotate the shaft 32, the process is repeated so that the fluid is taken into the pump, pressurized and discharged by the reciprocation of the secondary vane between the open and closed positions, which is caused by the rotation of the carrier ring 116 about its oblique carrier ring axis 246.

Figure 11A:
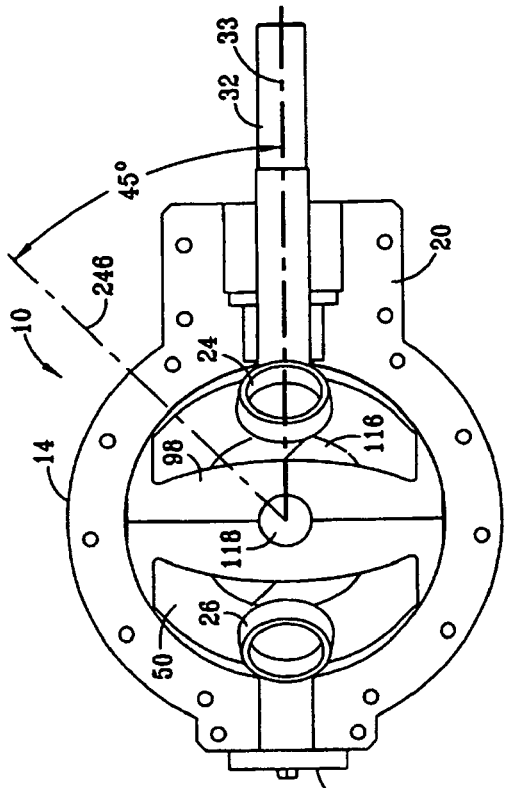
FIG. 11A is a perspective view of the pump of FIG. 1 shown with the upper half of the housing removed and the control lever in a 180-degree position.
Figure 11B:
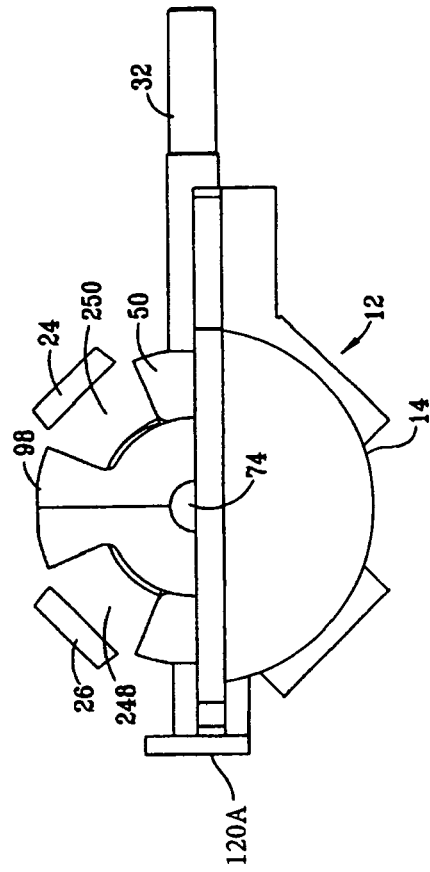
FIG. 11B is a front elevational view of the pump of FIG. 11A.
Figure 11C:
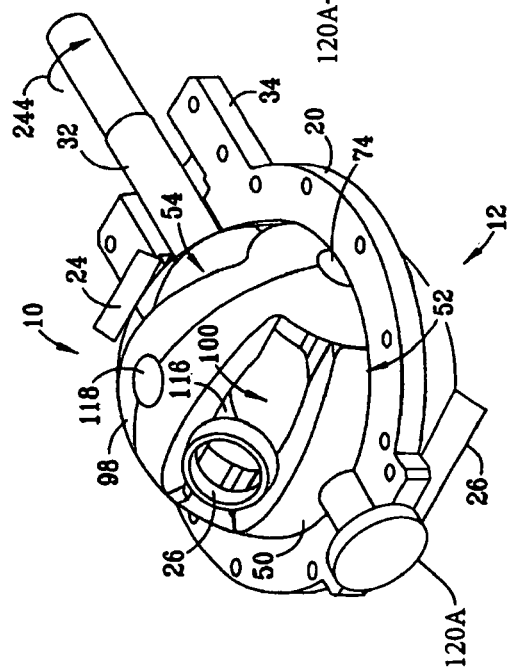
FIG. 11C is a top plan view of the pump of FIG. 11A.
Figure 11D:
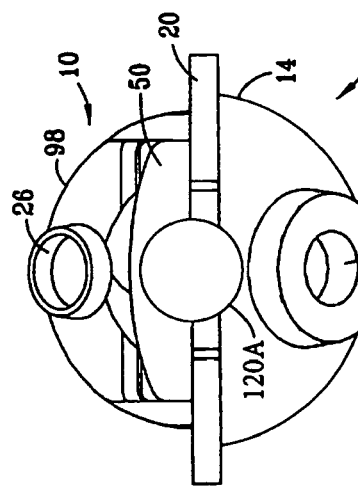
FIG. 11D is a side elevational view of the pump of FIG. 11A.

By rotating the fixed second shaft assembly 100 to different fixed positions, the flow of fluid through the pump 10 can be adjusted and even reversed without changing the direction of rotation of the input shaft 32. FIG. 11A shows the pump 10 with control guide 120A rotated so that the carrier ring axis 246 is oriented at an approximately 45 degree angle to the left of the primary axis 33, as viewed in FIG. 11C, or about 90 degrees from that orientation of the axis 246 as shown in FIG. 9C. In this position, the control plane 247 lies in a substantially horizontal plane that is generally the same or parallel to the plane of the flanges 20 which bisect the housing 12.

In the configuration of FIGS. 11A-11D, the forward port 26 of the upper housing 16 and the port 24 of the lower housing 14 serve as intake ports, while the port 24 of the upper housing 16 and the port 26 of the lower housing 14 serve as discharge ports.

FIGS. 12A-12E show sequenced views of the pump 10, with the control lever 120 rotated to the 180 degree position, as the input shaft 32 is rotated through 180 degrees of rotation. In FIG. 12A, the pump 10 is shown with the secondary vane 98A in the fully closed position against the primary vane 50A. The vane 98A is also in a fully open position with respect to primary vane 50B. Referring to FIG. 12B, as the input shaft 32 is rotated, as shown by the arrow, the secondary vane 98A begins to move to the open position with respect to the primary vane 50A. The space or chamber formed between the secondary vane 98A and vane 50A is in continuous communication with the port 26 of the upper housing 16 as it is moved to the open position. The increasing volume of this chamber as the shaft 32 is rotated, as shown in FIGS. 12C and 12D, draws fluid through the upper forward port 26. As this is occurring, the secondary vane 98B moves to the closed position with respect to the primary vane 50A forcing fluid between these vanes 98B, 50A through the forward port 26 of the lower housing 14.

FIG. 12E shows the pump after the shaft 32 is rotated 180 degrees. The secondary vane 98B is now in the closed position with respect to the primary vane 50A so that the process can be repeated. With the lever 120 in the 180 degree position, fluid is also discharged through rearward port 24 in the upper housing 16 and introduced through rearward port 24 of the lower housing 14 in the similar manner as that already described with respect to the forward ports 26. The ports 24, 26 remain in generally constant communication with one of the chambers created by the vanes 50, 98 during the entire stroke of the vane 98 between the open and closed positions.

Figure 13C:
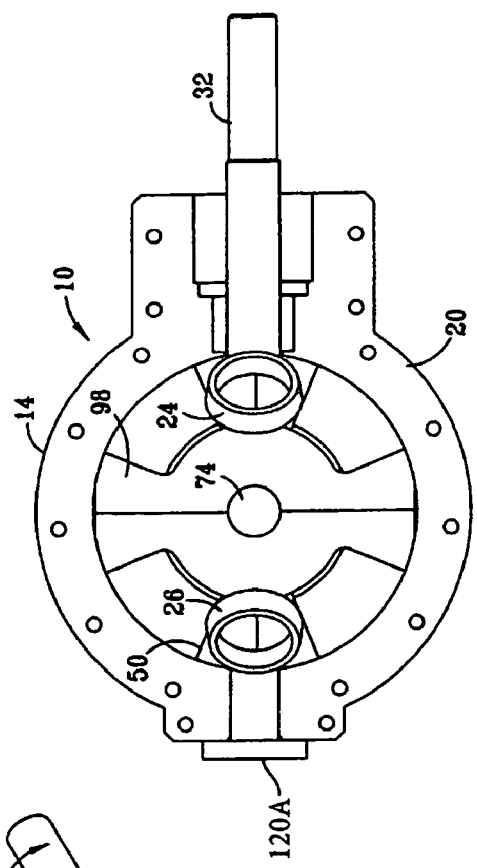
FIG. 13C is a top plan view of the pump of FIG. 13A.
Figure 13D:
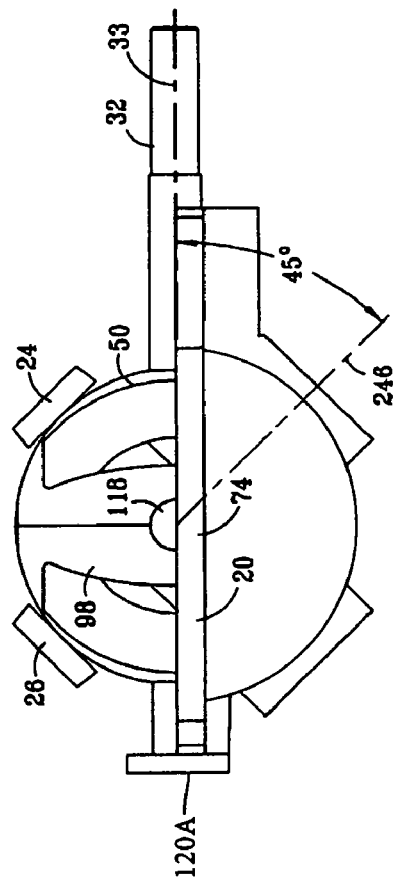
FIG. 13D is a side elevational view of the pump of FIG. 13A.
Figure 13A:
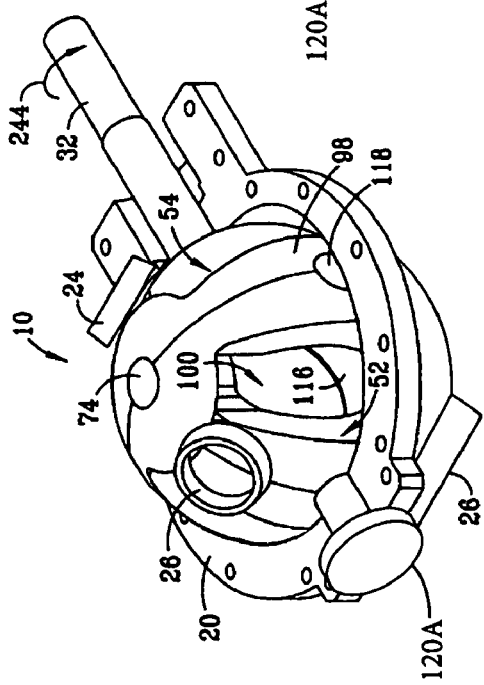
FIG. 13A is a perspective view of the pump of FIG. 1 shown with the upper half of the housing removed and the control guide in a neutral position.
Figure 13B:
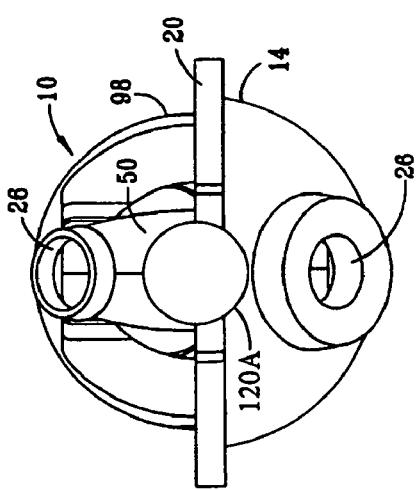
FIG. 13B is a front elevational view of the pump of FIG. 13A.

FIGS. 13A-13D illustrate the pump 10 in an intermediate or neutral mode, with control guide 120A oriented so that the carrier ring axis 246 lies in a plane perpendicular to the housing flanges 20 and is oriented at an angle of 45 degree below the primary axis 33, as viewed in FIG. 13D. In this orientation, the control plane 247 is in the 90 degree or vertical position, as seen in FIG. 8C. In this mode, the ports 24, 26 only communicate approximately 50% of the time with the chambers created by the vanes 50, 98.

FIG. 14A shows the secondary vane 98 in a center or intermediate position, with the primary vane 50 oriented so that it covers and seals the ports 24, 26. As the input shaft 32 rotates from this intermediate position, as shown in FIG. 14B, the port 26 of the upper housing 16 begins to communicate with the chamber between secondary vane 98B and primary vane 50A, and the port 26 of the lower housing 14 communicates with the chamber between the secondary vane 98A and primary vane 50A. As the secondary vane 98B is moved towards the open position with respect to the primary vane 50A, some fluid is drawn through the port 26 of the upper housing 16. In a similar manner, the secondary vane 98A is moved to the closed position with respect to the primary vane 50A so fluid therein is forced out of the lower port 26.

FIG. 14C shows the secondary vane 98B in the fully open position with respect to the primary vane 50A. The secondary vane 98A, which is hidden from view, is in the fully closed position with respect to primary vane 50A, with the closed space between the primary vane 50A and secondary vane 98A being in communication with the lower forward port 26 of the lower housing 14.

As the shaft 32 is rotated further, as seen in FIG. 14D, some fluid is forced out of the upper housing 16 through port 26 as the secondary vane 98B now moves to the closed position with respect to vane 50A. Fluid is also drawn in through the lower port 26 as the secondary vane 98A is moving to the open position in relation to the primary vane 50A.

FIG. 14E shows the pump 10 after rotation of the shaft 32 180 degrees from its original position of FIG. 14A. The secondary vane 98 is once again in the intermediate position, like that of FIG. 14A, and the process is repeated. With the control lever 120 in the 90 degree position, as described, the ports 26 of the lower and upper housing 14, 16 only communicate with the chambers defined by the primary and secondary vanes 50, 98 approximately 50% of the time. This results in equal volumes of fluid being both drawn and discharged through each of the forward ports 26 in the upper and lower housing during this neutral mode. The operation is the same with respect to the fluid flow through the rearward ports 24 in the lower and upper housing 14, 16. The net fluid flow through the pump 10 is therefore essentially zero.

By rotating the control lever 120 between the 0 degree and 180 degree positions, the fluid flow can be increased or decreased precisely in a smooth and continuous manner, and can be directed in either flow direction. This is due to the increased amount of time that the inlet ports and discharge ports communicate with the chambers 248, 250 formed by the vanes 50, 98 during the expansion and compression strokes, respectively, of the secondary vane 98. Thus, for example, as the lever 120 is rotated from the 90 degree or neutral position towards the 0 degree position of FIG. 10A, the length of time the forward port 26 of the upper housing 16 communicates with the chamber formed by the primary vane 50A and secondary vanes 98, as the secondary vanes 98 are moved to the closed position, is lengthened, resulting in more and more fluid flow through this port. As described previously, when the lever is at the full 0 degree position, the port 26 of the upper housing 16 is in communication with the chamber formed by the primary vane 50A and secondary vanes 98 during almost the entire compression stroke of the secondary vanes 98 with respect to the vane 50A so that full flow is achieved when the pump 10 is in this mode. Similar results in the reverse-flow direction are achieved by rotating the lever 120 between the 90-degree and the 180-degree position, which is shown in FIG. 12A.

Figure 22:
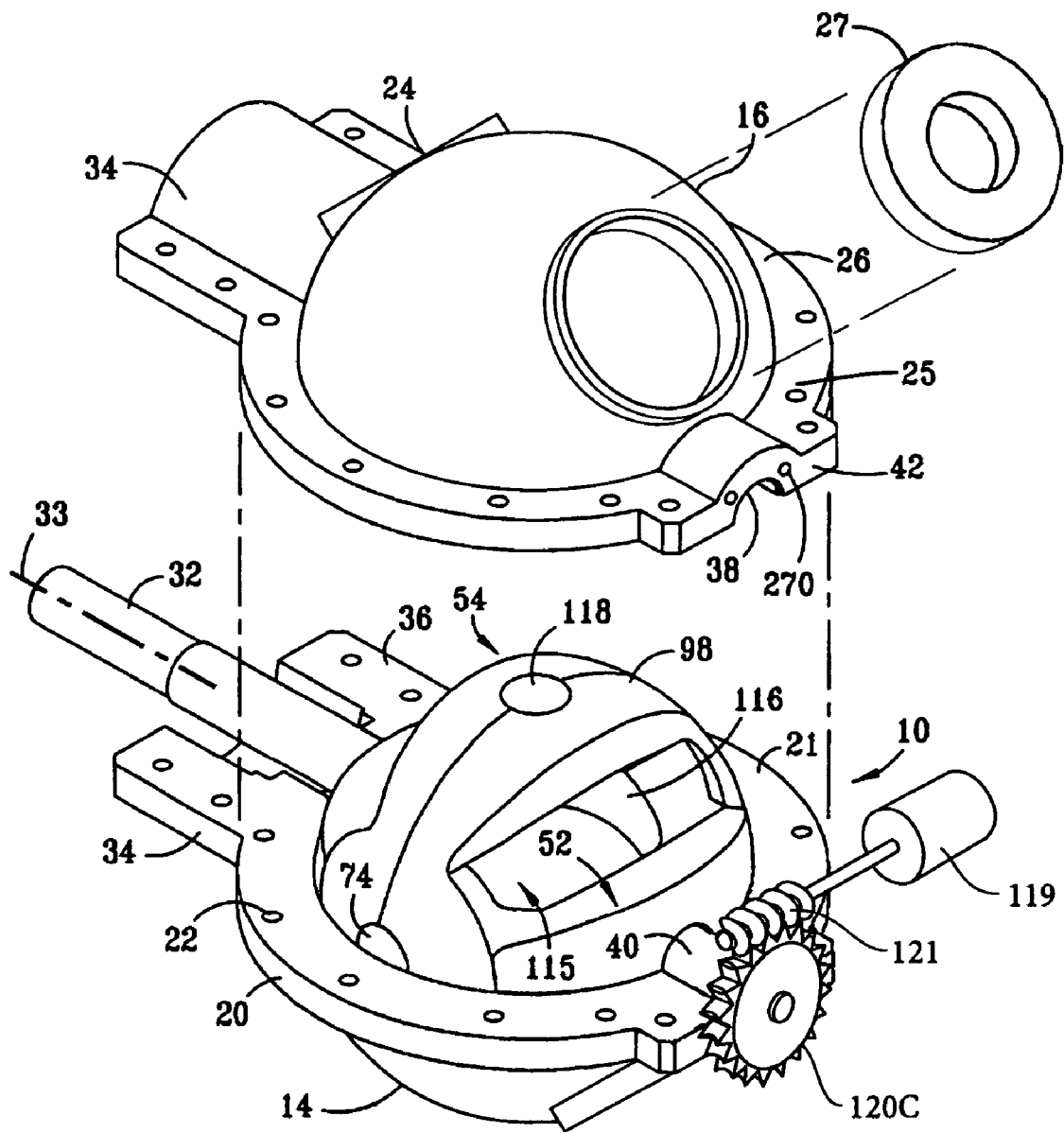
FIG. 22 is a front perspective view of a pump similar to FIG. 1 but showing the embodiment of a port insert.

Other means could be provided for rotating the second shaft assembly 100. For instance, the shaft 40 could be coupled to a worm and worm gear to rotate the second shaft to various positions. This in turn could be coupled to a controller that would cause the second shaft assembly to be rotated to automatically control and adjust the fluid flow or capacity of the pump 10. In this manner the flow capacity and even the direction of flow can be automatically adjusted remotely from the pump. A pump configured with this aspect of control of the second shaft assembly position can be seen in FIGS. 22, 24, and 25, where controller 119 turns worm gear 121 to rotate gear 120C attached to shaft 40. It should be recognized that other controller implementations could be used for remote control of the fixed shaft.

Figure 15:
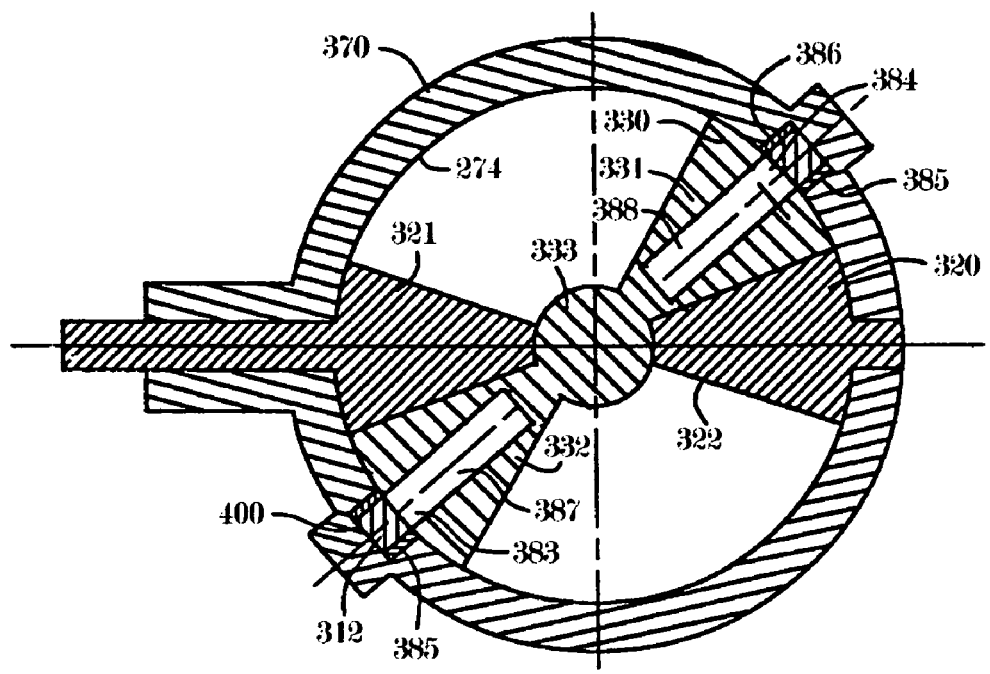
FIG. 15 is a detailed cross-sectional view of a spherical pump operating with an exterior carrier guide ring.
Figure 16:
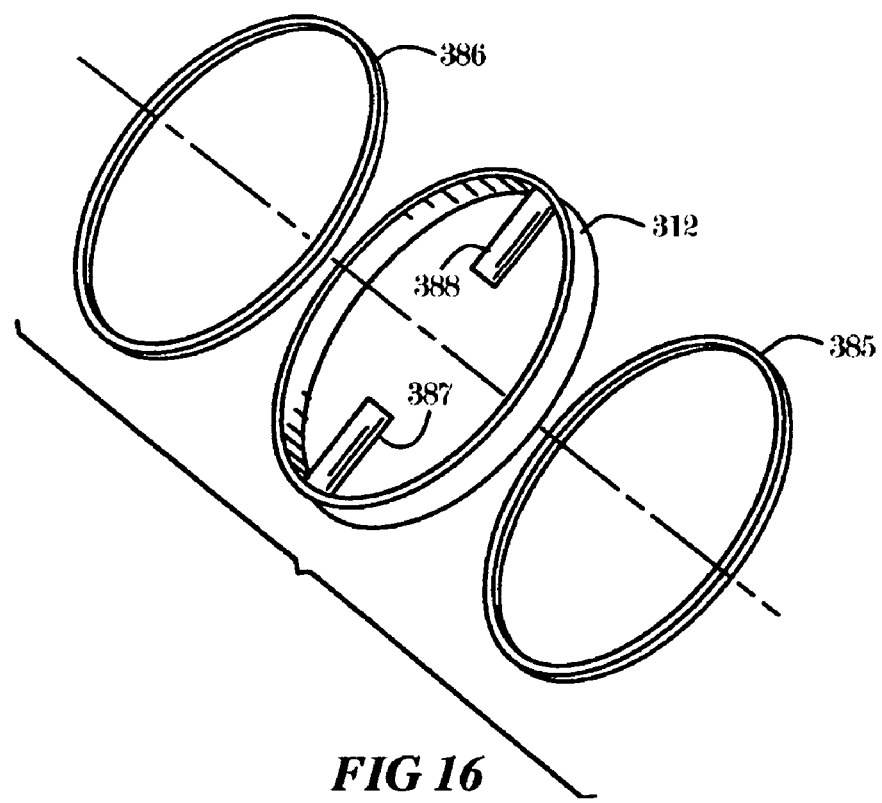
FIG. 16 is a detailed view of the exterior carrier ring of the device of FIG. 15.

The pump described above is based on an internal carrier ring assembly that guides the reciprocating action of the secondary vane. Alternately, these types of spherical pumps can have the guide carrier ring mounted in an exterior manner. U.S. Pat. No. 5,199,864 discloses a somewhat similar pump to that of U.S. Pat. No. 6,241,493 and also describes an embodiment (the "second embodiment") that uses an exterior carrier ring to guide the reciprocal motion of the vanes. In one particular alternative embodiment (the "second" embodiment) which is illustrated in FIGS. 15-16, a larger diameter collar 312 having inwardly protruding spindles 387 and 388 serves as the means for controlling reciprocation of secondary member 330 relative to rotation of primary member 320. The inside diameter of collar 312 matches the inside diameter of the spherical interior surface 274 of housing 370 in order to provide a flush spherical surface. The housing 370 is modified to define an angular raceway 400 between two halves of housing 370 for receiving collar 312 therein. Also received within raceway 400 are washer-like bearings 385 and 386 for enabling rotation of collar 312 within raceway 400. The housing 370 is formed in two halves that are joined by conventional means along raceway 400 for enabling assembly of collar 312 and bearings 385 and 386 within raceway 400. A central member 333 provides the pivotal engaging surface between primary member 320 and secondary member 330.

The other features of the structure and operation of this external carrier ring design are substantially the same as in U.S. Pat. No. 6,241,493 except, of course, changes in the interior surfaces of vanes 321, 322, 331 and 332 are preferably modified to accommodate central member 133. Similarly, the housing 370 of the second embodiment is modified to accommodate for raceway 400 therein, to produce the construction shown in FIG. 15. Many of the improvement embodiments of the instant invention have application in this type of exterior carrier ring design also.

Figure 21:
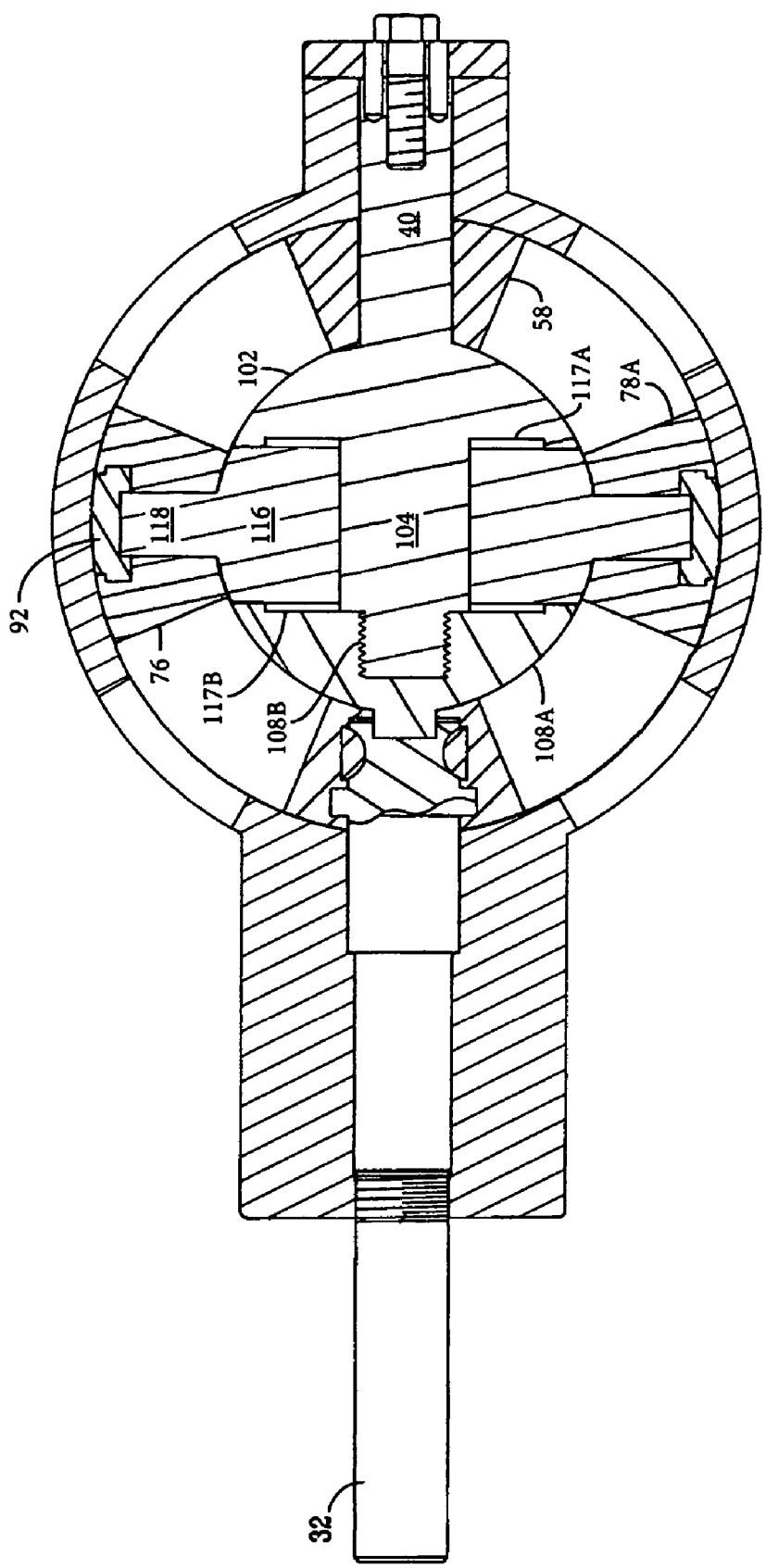
FIG. 21 is a cross-sectional view of the pump of FIG. 1, showing the embodiments of simplified mechanism, tight tolerancing and fluid flushing to improve use of the fluid machine as a blood pump.

The use of the prior art machines as described earlier was limited in its use as a blood pump, in that they either provided an undesirably complex mechanism and/or did not adequately address issues related to blood clotting. One key to avoiding clotting is to eliminate areas where blood flow can become stagnant. The instant invention is quite useful in that all or nearly all of the volume of a fluid chamber is expelled with each relative opening and closing of primary and secondary vanes, insuring that blood flow cannot become stagnant in the fluid chamber. Additionally, the surface of spherical interior 118 of housing 12 is continually being swept by the motion of the exterior portions of vanes 52, 54, and the mutually facing surfaces of vanes 52, 54 are repeatedly brought within close proximity to each other with every oscillating motion of secondary vane 54. In short, there is no blood-contacting surface within the housing 12 of pump 10 whereon flow can become stagnant, which feature greatly aids in the prevention of thrombosis. In a first embodiment for preventing blood clotting, FIG. 21 shows a simplified rotating mechanism adapted from the embodiment shown in FIG. 17. In this embodiment, the rotation of carrier ring 116 about the carrier ring axis is optionally slidingly facilitated by washer-shaped bearings 117A, 117B. To prevent the clotting of blood, which clots can migrate to other areas of the blood stream (thromboembolisms), the gap between carrier ring 116 and spherical shaft portion 102 and the gap between carrier ring 116 and end cap 108A, or optionally the gaps between the carrier ring 116 and bearings 117A, 117B and the gap between bearing 117A and spherical shaft portion 102 and the gap between bearing 117B and end cap 108A are preferably less than the approximate diameter of a red blood cell. Additionally, the gap between the cylindrical surfaces of pivot posts 118 and the corresponding recesses 92 of secondary vane halves 76, 78 is preferably less than the approximate diameter of a red blood cell. As can be seen, many of the moving parts shown in FIG. 17 have been removed or replaced in this embodiment, e.g. bearings 222 and fasteners 122, the latter of which have been replaced by threads 108B included on carrier ring shaft 104 to receive modified end cap 108A in a manner taught by Stecklein in U.S. Pat. No. 5,199, 864. This simpler mechanism reduces the complexity of the pump design, and is facilitated by the fact that the pump of the instant invention has a relatively low rotation rate of the input shaft 32, and alternatively may also be employed with the carrier ring on the outside of the housing interior, also as taught by Stecklein in U.S. Pat. No. 5,199,864.

Figure 17:
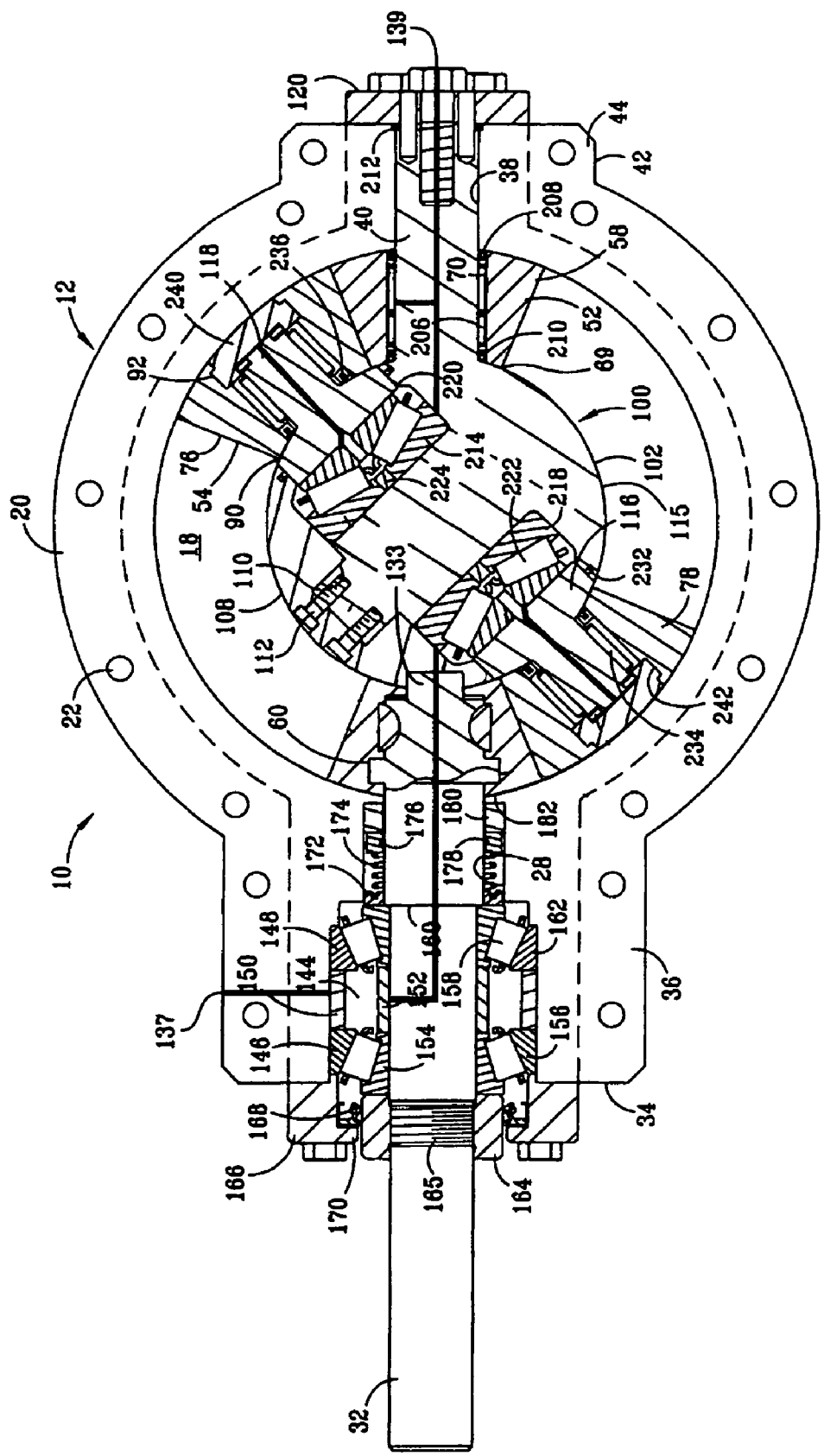
FIG. 17 is a detailed cross-sectional view of the pump of FIG. 1 showing added structure to improve rigidity and the addition of internal coolant-lubricant or flushing lines.

In a second embodiment for preventing blood clotting, FIG. 17 shows a mechanism for continuously flushing, cooling and/or lubricating moving interfaces of the instant invention, with a fluid flushing line running through the input shaft, filling the interior sections of the central ball 115, including one or more of the moving interfaces, and then flowing out through fixed shaft 40. This is shown as the dark lines beginning at point 137 and exiting shaft 40 at point 139. Alternatively, this fluid could flow in the opposite direction, feeding in through shaft 40 and out through point 137. The flushing fluid could be blood, blood plasma, or any of the various fluids known to be compatible with the human biological system, and could be supplied from fluid chambers within pump 10, from external connections to the vascular system, or from sources external to the body. Being biocompatible with the recipient, the flushing fluid could flow in limited amounts into the bloodstream of the recipient without adverse effects. This flushing mechanism may also be readily implemented in the simplified embodiment depicted in FIG. 21.

The use of the prior art machines as described earlier was also limited in its use as a blood pump, in that they cause excessive shear forces on the fluid as the fluid flows through the pump. One depiction of such excessive shear forces is provided in FIGS. 26A-26E, which approximately correspond to FIGS. 10A-10E of the description of the prior art, showing only the fluid volumes defined by chambers 301-304, as described in greater detail below with reference to FIGS. 20A-20E, and the upper and lower port fluid volumes 24A, 26A are defined by the interior of upper and lower ports 24, 26 respectively. As the input shaft 32 (not shown) rotates about its axis in the clockwise direction as shown in FIG. 20A, the fluid chamber 304 decreases from its maximum volume depicted in FIG. 26A near to its minimum volume as depicted in FIG. 26E. As the volume of fluid chamber 301 approaches its minimum, fluid in chamber 301 near upper port fluid volume 26A necessarily has a greater velocity (depicted by size of arrow 313) than the velocity 311 of the fluid furthest from upper port fluid volume 26A. This is because of the fact that the cross-sectional area provided perpendicular to the direction of fluid flow 313 near the port is roughly the same as the cross-sectional area provided perpendicular to the direction of fluid flow 311, while the cumulative flow of all points further from the port than the location of 313 pass through the position near arrow 313. This greater velocity 313 near the port interacts with the vane walls in a way that creates increased shear forces on the fluid in the vicinity of arrow 313.

Figure 27:
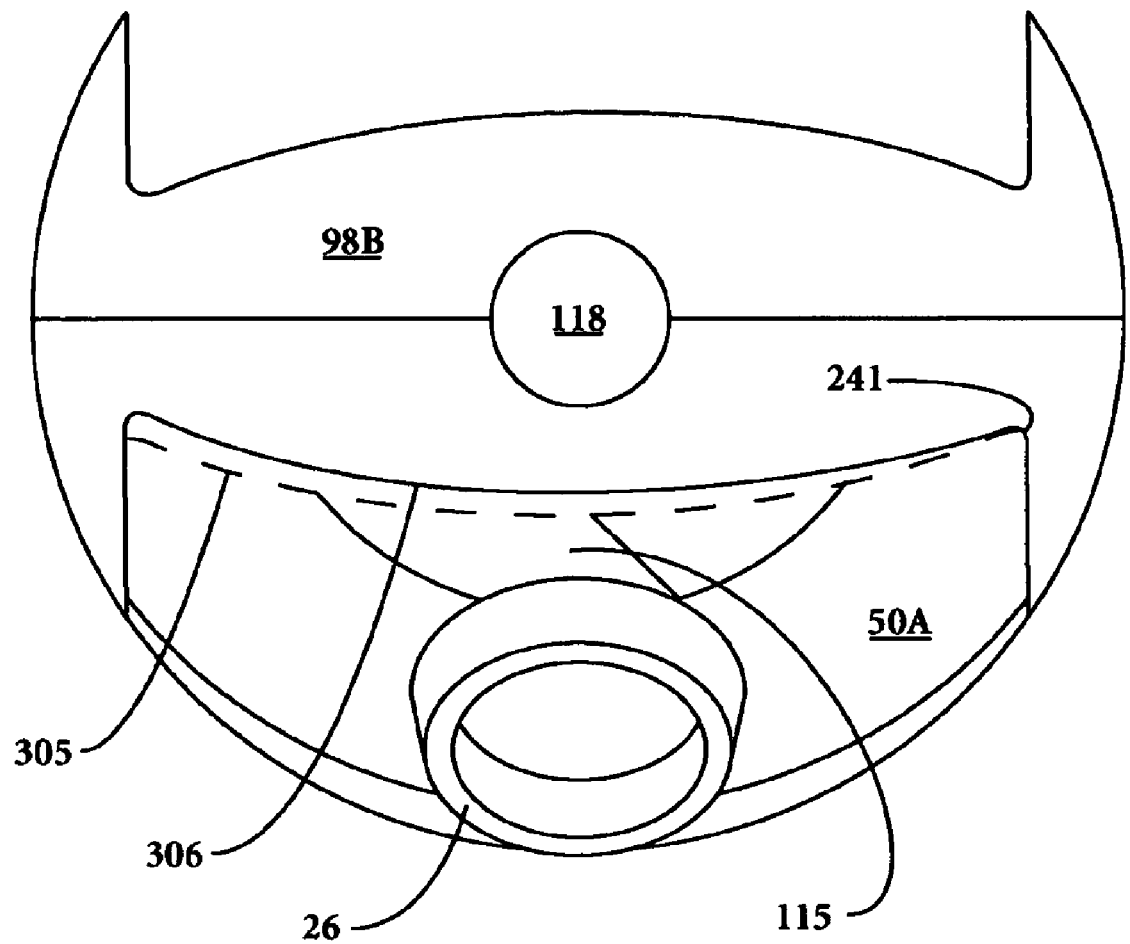
FIG. 27 is a perspective view of the secondary vane of the present invention, depicting a first aspect of altering the vane shape to reduce shear forces on the fluid.
Figure 28:
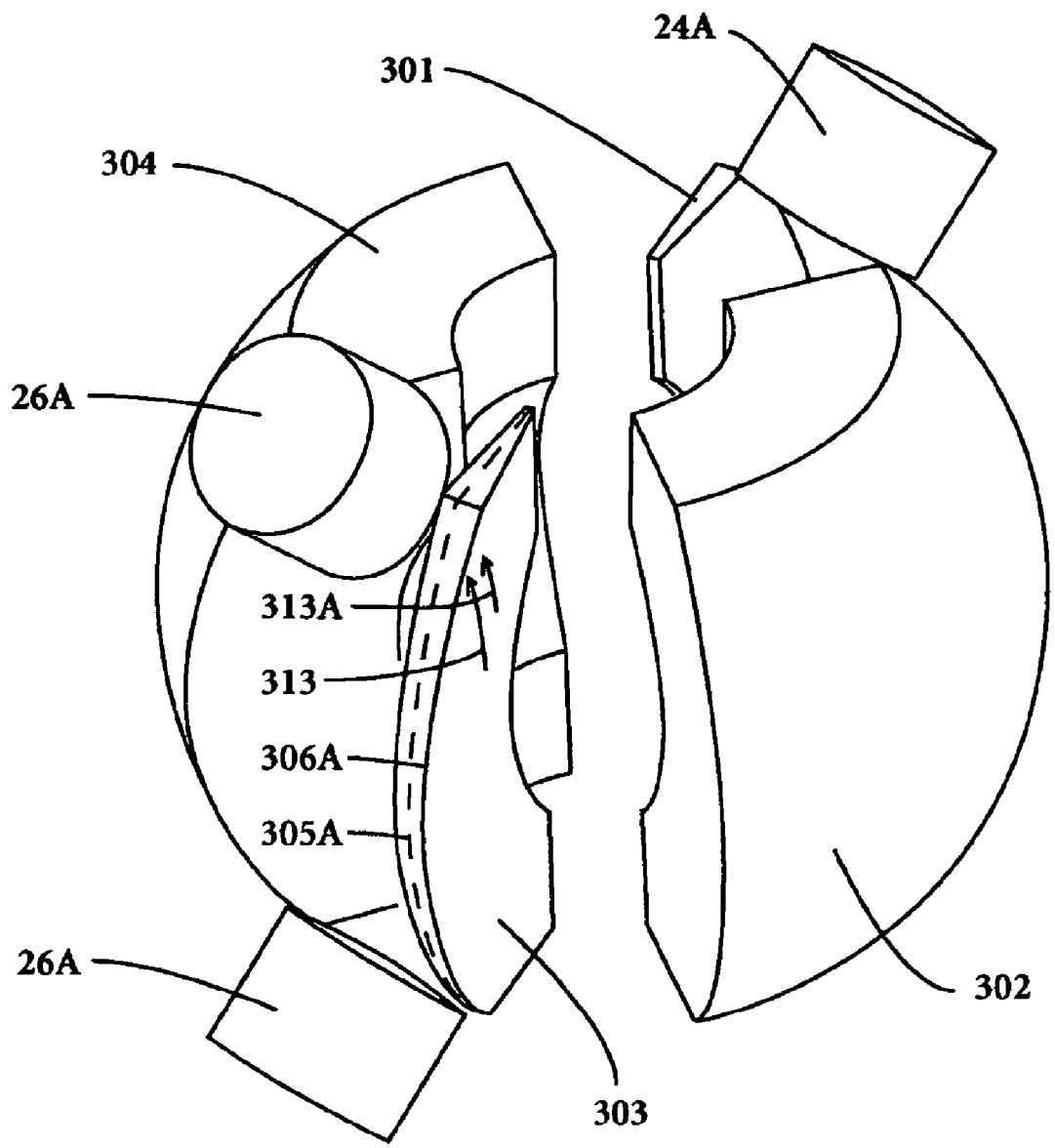
FIG. 28 is a perspective view of the fluid volumes shown in FIG. 26E, showing the embodiment of the vane shape being altered according to the first aspect depicted in FIG. 27 to reduce shear forces on the fluid.

To reduce the shear forces just mentioned, it is necessary to modify one or more surfaces of the vane from the standard shape taught in the prior art, which will be characterized generally as an "orange section", with two main planar faces that generally mate with faces on opposing vanes. In the aspects of sheer reduction hereafter mentioned involving alteration of the vanes, said alteration is generally a modification on (or of) at least one of the said vane faces. A first aspect of the instant invention that reduces the above-mentioned shear forces provides vane shapes such that the distance between proximal primary vane and secondary vane at locations nearer the port are greater than the distance between proximal primary vane and secondary vane at locations further from the port. One depiction of this embodiment is shown in FIG. 27, where a vane face of secondary vane 98B is altered according to surface 306, where the plane of the surface of secondary vane 98B facing the surface of primary vane 50A has been rotated slightly about an axis which is coincident with both point 241 and the center point of center ball 115, with the original surface 305 being represented with dotted lines for comparison. As shown in FIG. 28, the fluid near upper port 26A has a decreased velocity 312A, and therefore a decreased shear rate in the fluid at that location.

Figure 29:
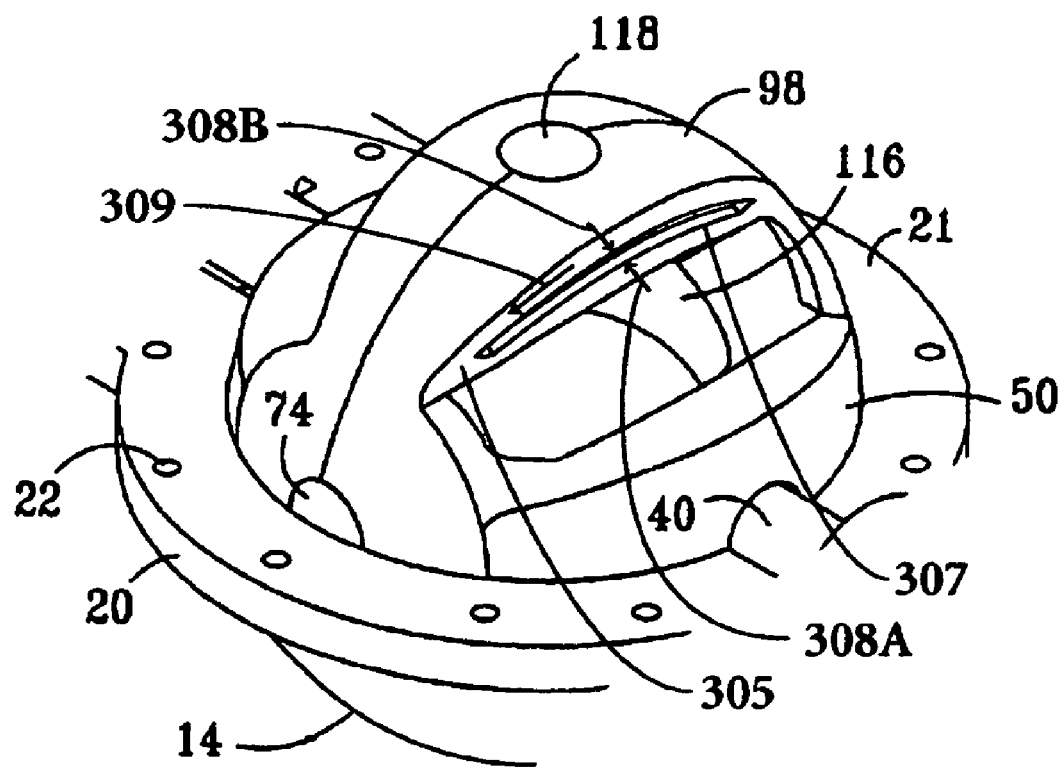
FIG. 29 is a perspective view of the secondary vane of the present invention, depicting a second aspect of altering the vane shape to reduce shear forces on the fluid.

With reference to FIG. 29, a second aspect of the instant invention for reducing shear forces alternatively provides at least one channel 307 in the vane surface 305, which channel allows fluid at points removed from the port to flow along paths 308A and 308B which are relatively perpendicular to and shorter than the more direct paths 309 along the surface 305 to the discharge port. The above two embodiments may be combined by providing channels 307 whose depth is tapered so that the depth of the channel 307 at a point closer to the port is deeper than the depth of the channel 307 at a point further from the port. Likewise, channel 307 can be tapered in its width so that it is larger near the port. As would readily be apparent to those skilled in the art, the same objective of reducing shear forces on blood as described above may be obtained by any of a variety of combinations of modifications in the shape, size or surfaces of primary vanes 50A, 50B and secondary vanes 98A, 98B.

Figure 30:
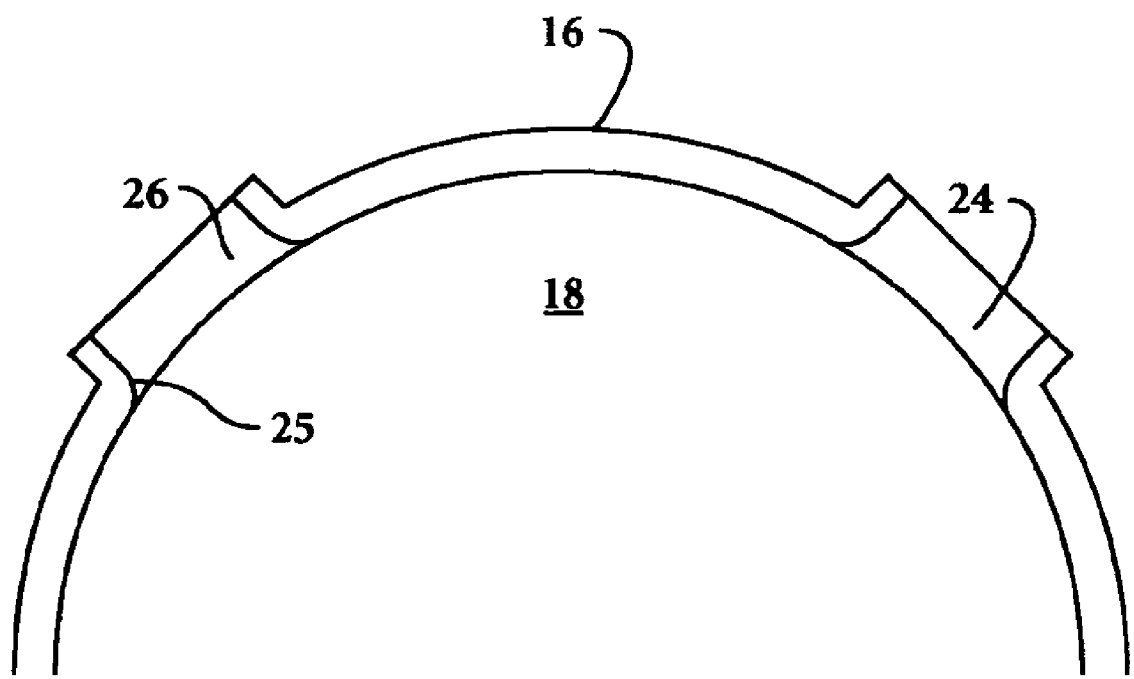
FIG. 30 is a cross-sectional view of a port of the present invention depicting a third aspect to reduce shear forces on the fluid involving altering of the transitional surface between the housing and a port.

With reference to FIG. 30, a third aspect of the instant invention for reducing shear forces additionally provides a curvilinear tapered portion 25 of one or more ports 24, 26 to reduce shear due to transitions between the housing surface and the interior of the port. Reduction of shear forces on fluid flowing between the housing interior 18 can be provided by a variety of different transitions between the housing interior 18 surface and the interior surface of the ports 24, 26 as would be apparent to those skilled in the art.

The present invention improves greatly over prior art devices in its use as an artificial heart or heart assist device. In one embodiment of the present invention, pump 10 is used as an internally implanted or extracorporeally connected assist or replacement to one or both ventricles of the human heart. In a preferred embodiment, pump 10 is sized to provide flow and pulsation rates that match the typical requirements of the recipient. In one example of this particular embodiment, and with reference to FIGS. 1, 3, 4, 21, a blood pumping system is sized to provide pulsatile flow for a recipient whose normal requirements are approximately five liters of blood flow per minute at a resting heart rate of 70 beats per minute. The pump of this example is formed with housing interior 18 of inside diameter 6.75 cm, center ball 115 of diameter 3.15 cm, an input shaft 32 of diameter 1.0 cm, secondary vane integral hinge portion 86 outside diameter of 3.75 cm and thickness of 0.5 cm in the vicinity of and axial direction of stub shaft 74, primary vane semicircular hinge portion 66 thickness of 0.675 cm in the radial direction of stub shaft 74, oblique angle of 45 degrees between longitudinal axis of the carrier ring shaft 104 with respect to the axis of fixed shaft 40, angle 321 of 44 degrees that the cross-sectional points nearest center ball 115 that the primary vanes 56, 58 and secondary vanes 76, 78 make with center of ball 115, and face angle 322 of 7 degrees that the vane faces make with respect to line 323 which intersects the center of ball 115 and the corner of the cross-section of primary vane nearest center ball 115. With this combination the pulsatile spherical pump of the instant invention can supply the required five liters/minute flow using input shaft rotational speeds of approximately 35 rpm, which rotational speed would also provide approximately 70 pulsatile "beats" per minute. This can be compared to rotational speeds of 4000-8000 for some current heart pumps.

For this embodiment, the materials of construction for the pump are selected from those known to have a high degree of hemocompatibility and biocompatibility in living systems, such materials including but not limited to titanium, pyrolytic carbon, Dacron, heparin, polyvinyl pyrrolidone- and polyacrylamide-based polymers, polyurethanes, and phosphorylcholines. In addition to these basic materials of construction some coatings can be applied to blood contacting surfaces or materials that can be added to the blood flowing through the system to increase the hemocompatibility of the blood-biomaterial interface. The materials so used include heparin, heparin proteoglycans, polyethylene-glycol-diisocyanate, saratin, clopidogrel (Plavix), triazolopyrimadine, prostaglandins, prostacyclin, prostaglandin E1, acenocoumarol (Sintrom; Novartis Pharma, Vienna, Austria), acetylsalicylic acid (aspirin) and derivatives of any of the foregoing.

For the case of this embodiment with internal implantation, the pump is implanted into the chest or abdominal cavity of the recipient and anchored in place by attachment via fasteners or tethers to the bones, muscles, sinews, and/or internal organs of the recipient. The surfaces of the pump may be either smooth or optionally porous to provide ingrowth of host cells to further anchor to and provide hemocompatibility and/or biocompatibility within the body. For a case where pump 10 is used as a biventricular assist device (biVAD), two each of ports 24, 26 of pump 10 are provided two inlet connections and two outlet connections for a total of four connections, which in turn are connected to the left and/or right ventricle, left and/or right atrium, aorta, pulmonary artery and/or another systemic or pulmonary artery or vein as best suited for the needs of the individual's case, and based upon whether the device is being used as a partial assist or total replacement for one or both ventricles of the heart. As a total replacement for both ventricles the four chambers of pump 10 provide unique equivalence in many ways to the four chambers of the heart. The flow rate of the device of this embodiment may be controlled by any combination of control of rotation rate of primary vane 52 or by means of flow control 124. For the latter in the case of internal implantation, the flow control 124 is preferably modified to a smaller profile from that shown in FIG. 1. An example of the smaller profile 120A is shown for example in FIGS. 9, 11, and 13. For the case where an electrical motor turns input shaft 32, the motor may either be attached locally to pump 10, or the motor may optionally be located remotely from pump 10, and connected to input shaft 32 via a rotary coupling or cable. Such remote operation may be desirable when there are space constraints, (e.g., in a small child) or to relocate the heat that may be generated by the motor remotely from pump 10.

As an alternative to the use of an external motor, the movement of vanes 52 and/or 54 can be powered electromagnetically. In this aspect, vanes 52 and/or 54 have, for example, permanent magnets imbedded in or on them in a way that does not interfere with the biocompatibility or hemocompatibility of pump 10. The vanes modified in this way are then moved via, for example, an electromagnetic field that is applied from within or external to the housing. This field is then sequenced in progressive locations in such a way as to maintain motion of vanes 52, 54 and therefore the pumping action of pump 10. In this aspect, input shaft 32 may be passive rather than a transferring member of the motive power, and may penetrate only the interior wall of housing 12 and end prior to penetrating the exterior surface of housing 12. Such a configuration may be advantageous in terms of compactness, which is desirable from the standpoint of implantation, as well as advantageous in reduction of the number of moving parts and simplification of manufacture, both of which are desirable in terms of reliability and cost. As another variation of this aspect with the carrier ring mounted external to spherical interior 18 in a manner similar to that described above for FIGS. 15-16, the carrier ring can be used as a stator to effect movement of secondary vane 54, which due to the previously described coupling to primary vane 52 via first and second pivotal axes both rotates the primary vane 52 and secondary vane 54 and causes the pivotal oscillation of secondary vane 52 with respect to primary vane 54, and pumping action with respect to inlet ports 24, 26 and discharge ports 24, 26 as described previously. With proper placement of said embedded magnets in vanes 52, 54 and appropriately configured magnetic fields from within or from outside of housing 12, rotation of primary vane 52 can be effected about primary axis 33, without the need for input shaft 32 to penetrate the interior wall of housing 12, and without the need for a carrier ring within spherical interior 18 or a carrier ring external to spherical interior 18. With this combination of proper placement of magnets and configuration of magnetic fields, the rotation of primary vane 52 about rotational axis 33 is stably maintained by said combination, and the pivotal oscillation of secondary vane 54 relative to primary vane 52 is also stably maintained by said combination. This has the dual advantages of reducing friction and reducing surface interfaces that may otherwise tend to difficulties in avoiding thrombosis.

The pulsatile blood pumping system can also be configured in a mode wherein the motor for rotating the first shaft is physically detached from the housing of the pump but either mechanically or electromagnetically linked to the first shaft. In this aspect of the invention the detached motor could be implanted in an abdominal cavity while the pumping system is implanted in the chest cavity of a living organism. Alternately the power required to rotate the first shaft can be supplied from outside the body (transcutaneously) by techniques such as radio frequency power transmitted across a receiving coil or via magnets coupled across a recipient's skin surface or through the skin (percutaneously) via an electrical line, mechanical cable or pneumatic tubing.

For the case of this embodiment with external use, the pump is located external to the recipient and mounted on a suitable carrier that is preferably mobile. Blood fluid is circulated with the inventive device to and from the recipient. The surfaces of the pump are preferably temperature controlled. Pump 10 can be configured as a biVAD in a manner similar to that described above for an implanted device, or can be configured to assist or replace one or both ventricles. The motor may either be attached locally to pump 10, or the motor may optionally be located remotely from pump 10, and connected to input shaft 32 via a rotary coupling or cable and/or a magnetic coupling. Such remote operation may be desirable to isolate heat generated by the motor away from the pump. Alternatively, thermal isolation may be accomplished using insulating material between the motor and pump. Also, in this case, ports can be relatively conveniently modified using changeable inserts as described for FIG. 24 below.

Figure 31:
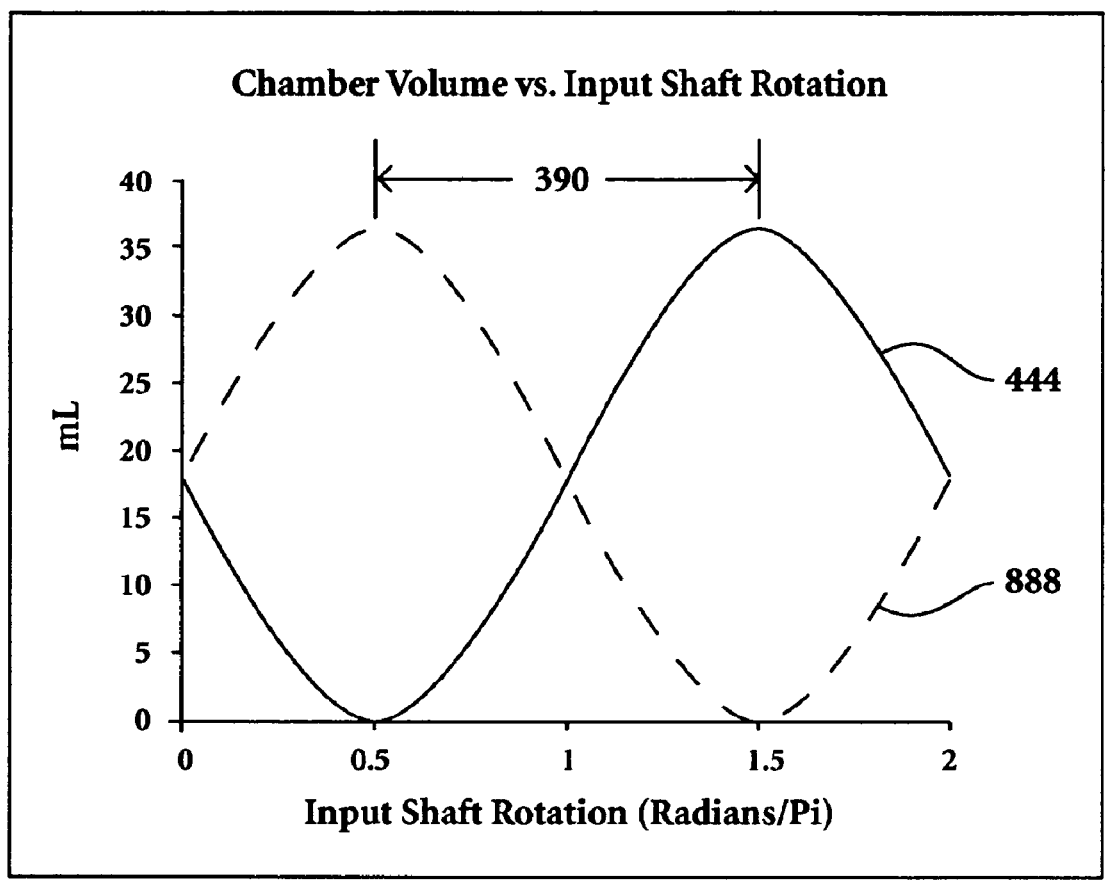
FIG. 31 is a graphical representation of the variation of the volumes of two fluid chambers as the input shaft is rotated in the pump in an embodiment for assisting or replacing the pumping of a human heart.

For the case of this embodiment where the vanes 56, 58, 76, 78 are similar in dimensions, FIG. 31 depicts the variation of the volume (in mL) of fluid chambers 301 (curve 444), and 302 (curve 888) as primary vane 52 is rotated about the axis of input shaft 32. As previously explained herein, however, alterations can independently provide differences in flow rates through one or more of the fluid chambers. Returning to the specific case depicted in FIG. 31, the volumes of the chambers 301, 302 vary sinusoidally with a maximum volume of 36.2 ml as the primary vane 52 is rotated one full revolution (2·radians) about the axis of input shaft 32 at a rate of 35 rpm. In this embodiment, the output flow of chambers 301, 303 have coincident peaks and troughs and are provided with a first common outlet, and the output flow of chambers 302, 304 have coincident peaks and troughs and are provided with a second common outlet. Such combined output and input flows may be useful, for example in the case where pump 10 is being used as a left ventricular assist device (LVAD) or as a right ventricular assist device (RVAD). Separating the two inlet flows and two outlet flows would of necessity provide a different transient flow profile, while not detracting from their pulsatile nature. Since the volume variations have offset timings as depicted by distance 390 in FIG. 31, the flow rates also vary with offset timings, and the depicted embodiment provides two flow pulses of 72.4 ml, one each from the first and second common outlets, with each revolution of the primary vane 52 about the input shaft 32, giving an average flow rate of about 5 liters per minute, and approximating a heart beat rate of 70 pulses or "beats" per minute, which matches the normal requirements of the example recipient above. Both flow rate and pulsation rate can be increased to the maximum anticipated need of the recipient by increasing the rate of rotation of input shaft 32. In the preferred embodiment for the case of the pump being used to assist or replace both ventricles, the output from the four chambers is separated and the ratio of magnitudes of flow through the first and second outlets is adjusted as described in the paragraphs below to better reflect the natural difference between the flow of the right and left ventricles of the heart, which is typically about 20% higher in the left ventricle. In this preferred embodiment for assisting or replacing both ventricles, the present invention can provide the distinction of providing two substantially simultaneous pulse peaks (discharge surges) from the same device, which is highly advantageous from a physiological standpoint. Additionally, the device provides two substantially simultaneous pulse troughs (intake surges), which is also highly advantageous. Furthermore, the device provides at least one pair of simultaneous intake and discharge streams. In an optional embodiment when this device is used as a heart assist device or ventricular assist device, electronic sensors and control circuitry is used to time the pump rotation so that flow pulsations delivered by pump 10 coincide, with or without peak-to-peak offset, flow pulsations of one or both of the heart ventricles of the recipient. Still further, the shape of a transient flow curve corresponding to any chamber of pump 10 may be modified by appropriately placing a flow element with capacitive (e.g., elastic properties) and/or resistive characteristics in communication with said chamber. It is apparent without further explanation, that this embodiment providing a pump capable for being used as an artificial heart or heart assist device may also include any combination of features of the above- and below-mentioned embodiments to reduce shear stresses on the blood being pumped through the machine, vary the ratio of flow rates between chambers, flush components and/or provide tight tolerances between moving parts.

A significant advantage of this embodiment of the present invention is that it does not require valves in the traditional sense. Valves of prior art artificial hearts are prone to wearing out and to becoming calcified, which are both disadvantageous for a life-sustaining device. Another advantage of the present invention is that it can be sized to match both the normal flow rate and provide the pulsatile flow that mimic the natural characteristics of the recipient's heart. Another advantage is that the present invention can be operated at relatively low rpm, simplifying motor requirements and reducing the potential for wear of moving parts. Still another advantage is the relatively small size of the pump.

Figure 18:
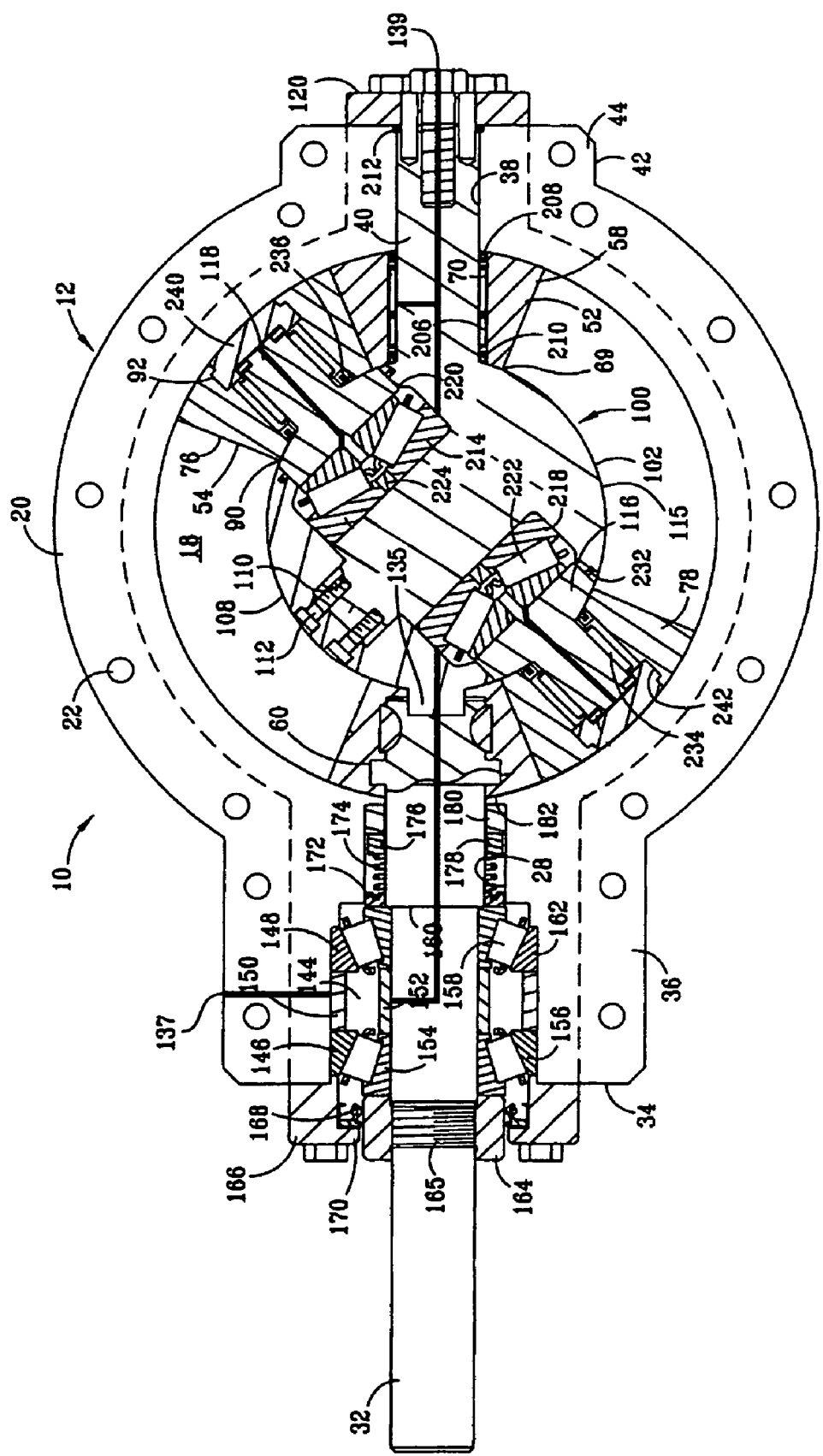
FIG. 18 is a detailed cross-sectional view of the pump of FIG. 1 showing a different embodiment of added structure to improve rigidity and the addition of internal coolant-lubricant or flushing lines.

For use as a blood pump the pulsatile blood pumping systems with internal carrier rings described as part of the instant invention can have alternate designs with respect to the internal sphere. One design is to have is no contact between the vanes and both the internal sphere and the housing of the machine. With no internal contact between those internal components the pulsatile blood pumping system just described has the potential for long life during use. In constant use however instabilities can occur that result in vibration of the internal structures, causing for example unwanted interference between the exterior surfaces of vanes 52, 54 and the interior of housing 12 and/or the exterior surfaces of spherical portion 102 and the end cap 108. Accordingly a second design provides for improved rigidity of the internal structure of the pump. FIG. 17 shows this second design that significantly improves the rigidity of the internal structure of the pump. At the interior end of rotating shaft 32 a nipple 133 is extended into the end cap 108 and rotatably attached by means of a suitable bearing assembly (not shown). This extended nipple provides significantly improved rigidity to the design without significantly increasing the load on the rotating shaft. The extended nipple also allows the inclusion of a pathway for a lubricating coolant fluid or a flushing fluid to and through the central ball 115. Alternately the desired rigidity can be supplied by an extension 135 from the central ball 115 attached rotatably to input shaft 32 as shown in FIG. 18. It should be recognized that the rigidity desired from this change could also be achieved by related mechanical implementations, such as a sleeve extending from the central ball 115 and encircling the input shaft 32 with appropriate bearing assembly to maintain the shaft as rotatable, or such as a rotatable coupling between the primary vane 50A and end cap 108. These latter two versions of the rigidity solution are not shown in the drawings.

In another embodiment to inhibit fluid leakage between chambers seals are provided between the two vanes and the central ball and seals are also provided between the two vanes and the pump housing. Also to inhibit fluid leakage and with reference to FIG. 3 and FIG. 4, preferably seals are provided (but not shown) between the stub shaft 74 and the recesses 94; likewise seals are provided (but not shown) between the stub shaft 96 and the recesses 72, between the outer side edges 73 of primary vane halves 56, 58 and inner side edges 89 of secondary vane halves 76, 78, and between narrow ridges 83 of the secondary vane halves 76, 78 and the hinge portions 66, 68 of primary vane halves 56, 58. It should be recognized that such seals could be made from high performance plastic or elastomeric materials. Alternatively, the seals of this embodiment may be brush seals or labyrinth seals, both of which are commonly known.

Figure 19:
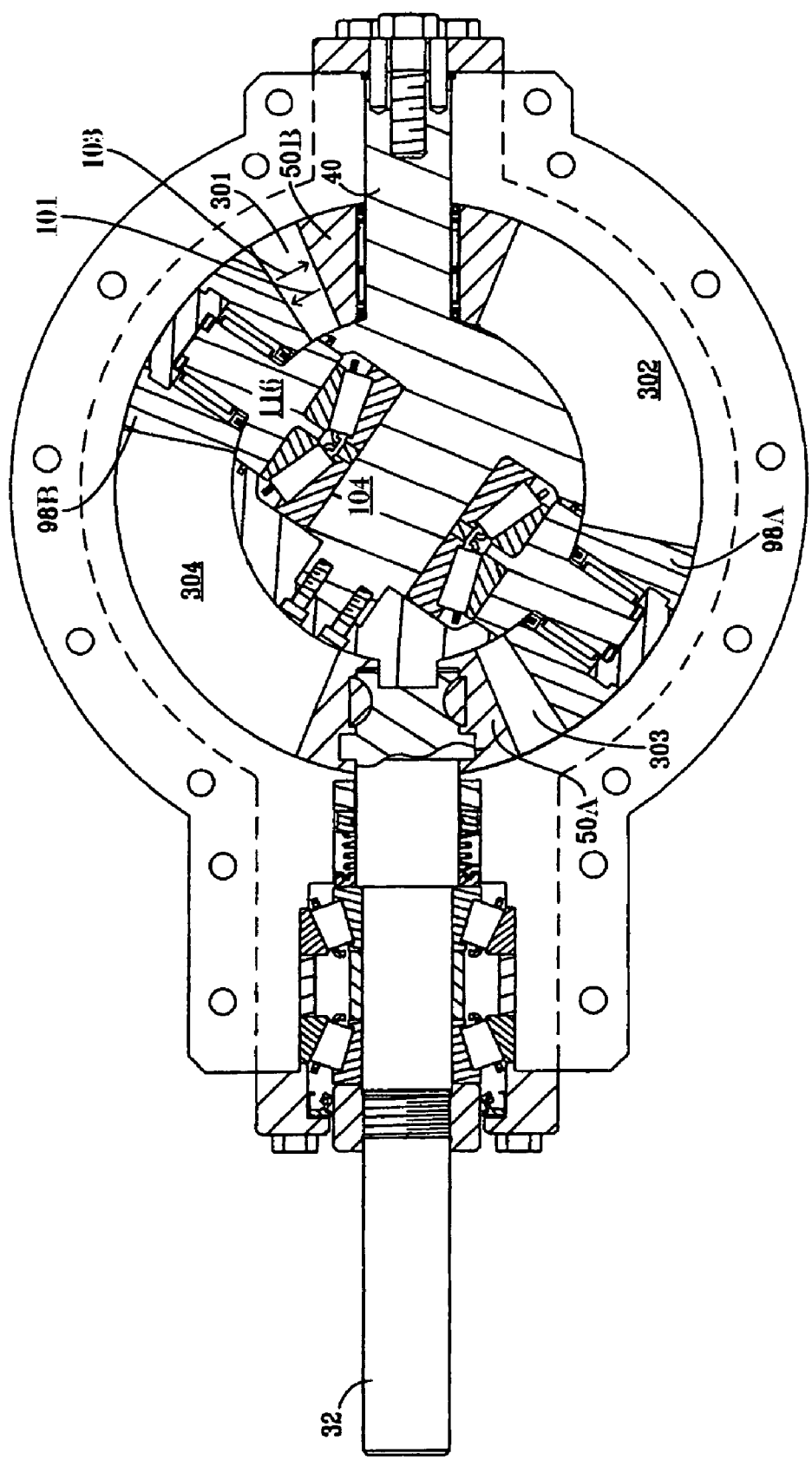
FIG. 19 is a cross-sectional view of the pump of FIG. 1, showing an embodiment providing balanced forces across a secondary vane as the secondary vane approaches the relatively closed position with respect to the primary vane.

The use of the prior art machine as described earlier was limited in that it did not provide for balancing forces upon the secondary vane as it neared the relatively closed position with respect to the primary vane. As shown in FIG. 19, secondary vane 98B is approaching the relatively closed position with respect to primary vane 50B. The pressure of the fluid being pressurized in chamber 301 exerts a force depicted in the general direction 101, which pressure force was not balanced in prior art machines by the force depicted in the general direction 103 which latter force is due to the slowing of momentum of secondary vane 98B. In an embodiment of the present invention, the weight or density of secondary vane 98B is adjusted to balance momentum force 103 with pressure force 101, which lowers the wear on the interfacing surfaces and bearings between secondary vanes 98A, 98B and the carrier ring 116, and between the carrier ring 116 and the carrier ring shaft 104. This adjustment of weight or density may be accomplished by any combination of the following means: selection of materials of differing densities or composite combination of materials which combination achieves differing densities, and/or void spaces in the vanes.

The pulsatile spherical blood pumping system can be configured to flow two different fluids, such as for example oxygen-rich blood and oxygen-poor blood through the same pump as can pump one fluid. FIGS. 20A-20E show sequenced views of the pump 10 in operation with the control lever 120 in the 0 degree position as the input shaft 32 is rotated through 180 degrees of revolution and while simultaneously flowing two fluids through its interior. In this configuration, the single pump 10 acts as two pumps simultaneously, and therefore is able to do the work of two pumps while occupying much less space than two pumps. For conceptual convenience, the majority of the lower housing half 14 is not shown. As discussed with FIGS. 10A-10E, motion of the input shaft 32 causes each secondary vane 98A, 98B to reciprocate or move back and forth between a fully open position and a fully closed position with respect to primary vanes 50A, 50B. Chamber 301 is defined as the space between primary vane 50B and secondary vane 98B, chamber 302 is defined as the space between primary vane 50B and secondary vane 98A, chamber 303 is defined as the space between primary vane 50A and secondary vane 98A and chamber 304 is defined as the space between primary vane 50A and secondary vane 98B.

In the depicted embodiment, simultaneous flow of two fluids is accomplished by connecting upper port 24 to a first fluid source and lower port 26 to a second fluid source. Lower port 24 acts as an outlet for the first fluid and upper port 26 acts as an outlet for the second fluid. FIG. 20F shows that concept by showing the port openings only. First fluid 196 enters upper port opening 24 and exits lower port opening 24. Second fluid 196 enters lower port opening 26 and exits upper port opening 26. In the sequences shown in FIGS. 20A-20E, the first fluid flows from the first fluid source through upper port 24 into chamber 301, and from chamber 302 out of lower port 24. Simultaneously, the second fluid flows from the second fluid source through lower port 26 into chamber 303, and from chamber 304 out of upper port 26. This separation of flows of the two fluids is facilitated by the previously discussed seals between the vanes and the interior of the housing 12, between the vanes and the exterior of the central ball 115, and between the primary vanes 50A, 50B and secondary vanes 98A, 98B.

In similar manner as described for FIGS. 20A-20E, as the input shaft 32 is rotated through another 180 degrees of rotation, first fluid flows from the first fluid source through upper port 24 into chamber 302, and from chamber 301 out of lower port 24. Simultaneously, the second fluid flows from the second fluid source through lower port 26 into chamber 304, and from chamber 303 out of upper port 26. In the depicted embodiment, chambers 301 and 302 transfer only the first fluid through upper and lower ports 24, and chambers 303 and 304 transfer only the second fluid through upper and lower ports 26.

As an example of an embodiment that is particularly useful, as an alternative to using a motor to drive pump 10, motive power for rotating input shaft 32 of pump 10 may be provided by flowing a first fluid under pressure from a first fluid source in the above configuration through upper port 24, which alternatingly powers the expansion of chambers 301 and 302 which in turn rotates primary vane 50 about input shaft 32. Chambers 303 and 304 then draw in and expel blood fluid from and to the recipient. Advantages of this embodiment include reduced space and elimination of heat that would otherwise be generated by an electric drive motor. This first fluid is preferably a biocompatible liquid, but may also include inert and/or humidified gas.

The ability to separately control the flow of two different blood fluid streams in the same pulsatile blood pumping systems is an important concept of the instant invention. In another embodiment of the instant invention, FIGS. 23A-23E show sequenced views of the pump 10 in operation with the control lever 120 in the 0 degree position as the input shaft 32 is rotated through 180 degrees of revolution and while simultaneously flowing two fluid streams at two different flow rates through its interior. For conceptual convenience, the majority of the lower housing half is not shown. As discussed with FIGS. 20A-20E, motion of the input shaft 32 causes each secondary vane 98A, 98B to reciprocate or move back and forth between a fully open position and a fully closed position with respect to primary vanes 50A, 50B, varying the volumes of chambers 301-304 as previously defined. Simultaneous flow of multiple fluid streams at different flow rates is accomplished by rotating ports 26 about the axis of input shaft 32 in relationship to ports 24. In the depicted embodiment, ports 26 are rotated 20 degrees about the axis of input shaft 32. Upper port 24 is connected to a first fluid source and lower port 26 to a second fluid source. Lower port 24 acts as an outlet for the first fluid and upper port 26 acts as an outlet for the second fluid. In this embodiment, the first and second fluid may be either the same fluid or different fluids. In the sequences shown in FIGS. 23A-23E, the net flow rate of second fluid from the second fluid source through lower port 26 has been decreased, due to the altering of the position of ports 26 with respect to the opening and closing of the secondary vanes 98A, 98B with respect to primary vanes 50A, 50B, in a manner similar to that previously described when second shaft assembly 100 is rotated to various fixed positions as described for the sequences in FIGS. 1A-10E, 12A-12E, 14A-14E.

Figure 24:
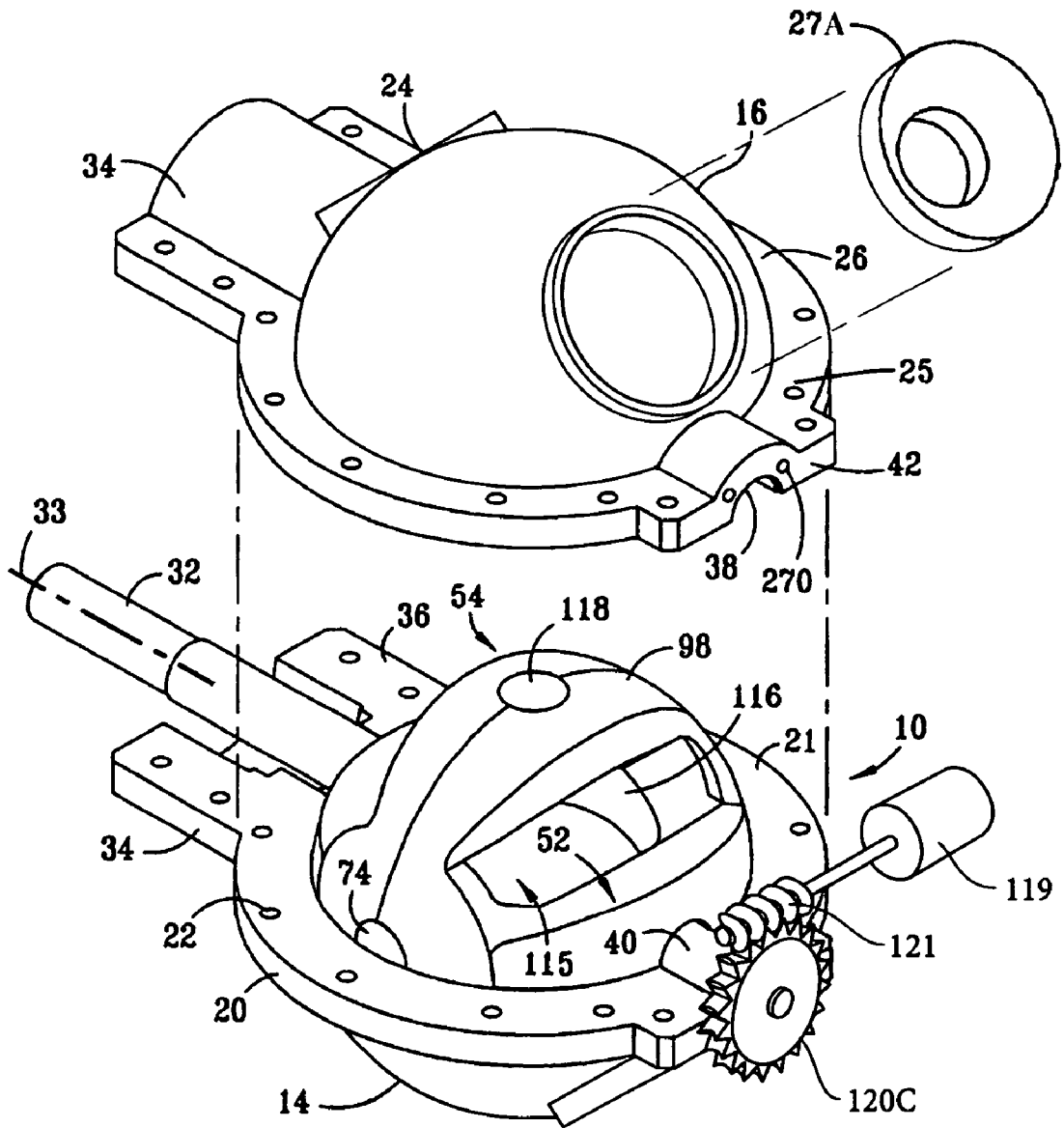
FIG. 24 is a front perspective view of a pump similar to FIG. 1 but showing the embodiment of an eccentric port insert.
Figure 25:
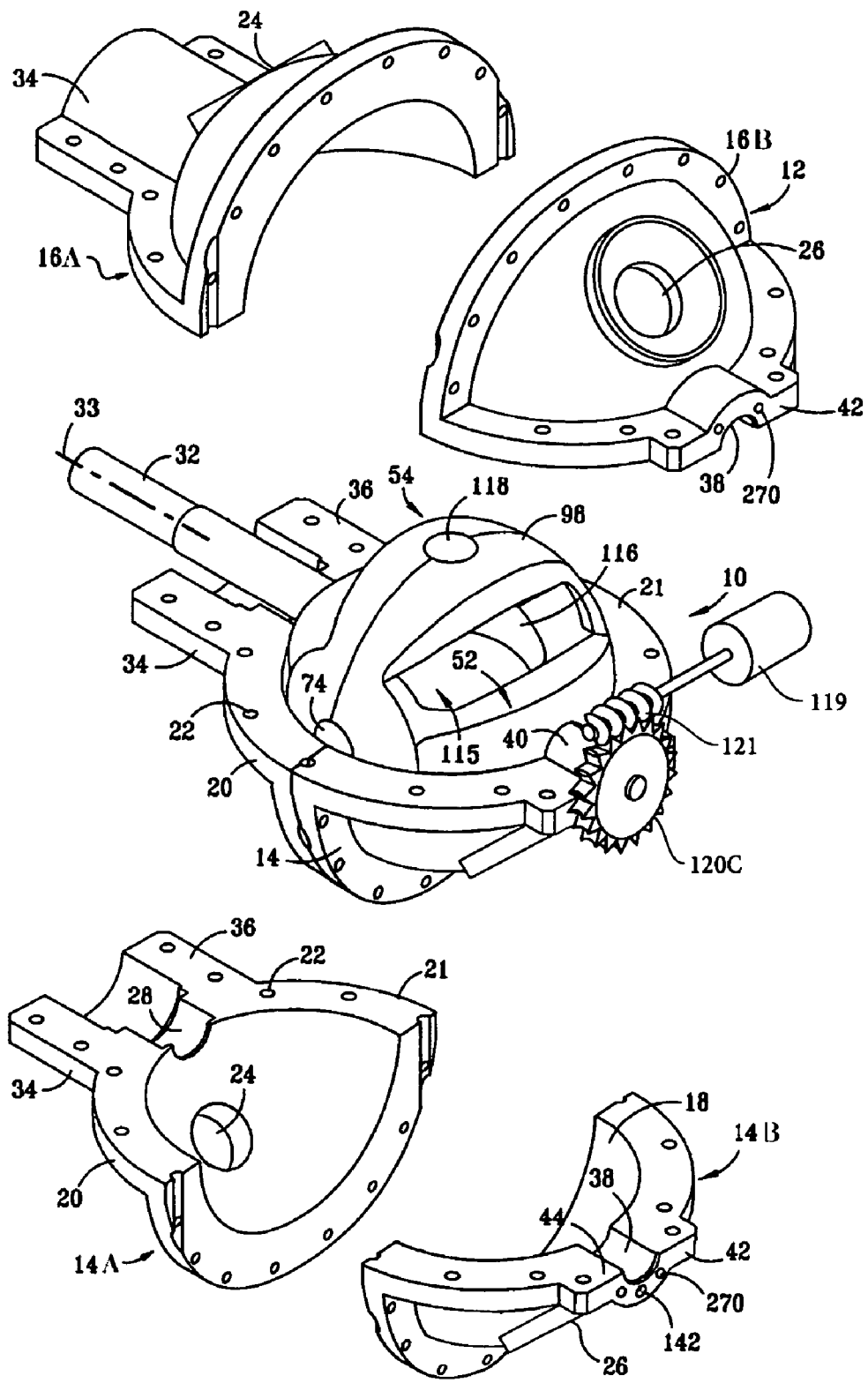
FIG. 25 is a front perspective view of a fluid pump, shown with the upper and lower halves of the housing of the pump exploded away and divided into quarters, and internal components of the device removed.

In this embodiment, rotating the position of ports 26 about the axis of the input shaft 32 in relationship to ports 24 may be accomplished through several means. One such means would be to provide eccentric port inserts 27A as shown in FIG. 24. Both upper and lower ports 26 are rotated in this manner to a similar extent, to avoid fluid locking of the pump. The shapes provided for the openings of port inserts 27A could obviously be selected from a great variety (e.g., oblong) to effect various alterations of flow through said port openings. This insert means may also be alternatively employed with the carrier ring on the outside of the housing interior, as taught by Stecklein in U.S. Pat. No. 5,199,864. As shown in FIG. 25, another such means is to divide housing halves 14, 16 into quarter sections 14A, 14B, 16A, 16B along the plane perpendicular to the axis of input shaft 32 and intersecting the center of center ball 115. Flanges are provided to each quarter section to allow sealing of quarter sections 14A, 16A to quarter sections 14B, 16B after rotation of ports 24 to a new fixed position (for example, by rotating quarter sections 14B, 16B about the axis of input shaft 32). Additional means of rotating ports 24 about the axis of input shaft 32 relative to ports 26 may also be employed, as readily apparent to those skilled in the art. This embodiment may be implemented independent of or in combination with any number of the above-mentioned embodiments that provide for flow of multiple fluids, that provide for removal of heat from the interior of the pump, that provide for changeable ports, or that provide for stabilization of the structure.

Additional embodiments that independently vary the relative flow rates through at least two ports are possible. These include altering the shape or one or more face angles of any of the vanes 50A, 50B, 98A, 98B, which shape altering may optionally be accomplished by plates driven by hydraulic bladders, providing corresponding adjustments to the flow of fluid(s) through chambers 301-304. Another embodiment includes providing a path for relative one-way flow between chambers. The flow path may be through or around a vane, and is tapered or valved to preferentially allow flow in one direction.

Traditional centrifugal or axial flow pumps used in blood pumping applications are moving blood fluids vigorously through the pump during the entire cycle of pumping. In the pump described and claimed in the instant invention blood fluids are drawn into one of the fluid chambers through an intake port and held temporarily until the fluid chamber approaches a discharge port where the blood fluid is discharged as the chamber closes. In this manner the pulsatile blood pumping system described more closely resembles the action of a human heart, which brings in blood and temporarily holds it before discharging.

Having thus described the present invention by reference to certain of its preferred embodiments, it is noted that the embodiments disclosed are illustrative rather than limiting in nature and that a wide range of variations, modifications, changes, and substitutions are contemplated in the foregoing disclosure and, in some instances, some features of the present invention may be employed without a corresponding use of the other features. Many such variations and modifications may be considered obvious and desirable by those skilled in the art based upon a review of the foregoing description of preferred embodiments. Accordingly, it is appropriate that the appended claims be construed broadly and in a manner consistent with the scope of the invention.

The invention claimed is:

1. A method for circulating at least one blood fluid through a living organism in a pulsatile manner with a pulsatile blood pumping system comprising the steps of:

providing a housing having a wall defining a generally spherical interior, the housing having at least one intake port opening in communication with said interior of said housing and at least one discharge port opening in communication with said interior of said housing through which said at least one blood fluid flows;

connecting said at least one intake port opening and said at least one discharge port opening to enable the circulation of said at least one blood fluid through said living organism;

rotating a first shaft mounted for rotation relative to said housing about a primary axis;

rotating at least one primary vane disposed within the interior of the housing that rotates about said primary axis;

providing at least one secondary vane disposed within the interior of the housing and mounted to said primary vane on a first pivotal axis; and rotating said primary vane about said primary axis with said secondary vane pivotally oscillating between alternating relatively open and closed positions with respect to said primary vane, the housing, the primary vane, and the secondary vane defining a at least one fluid chamber for containing blood fluid within the housing interior having a volume that varies as the primary vane is rotated about the primary axis.

2. The method for circulating at least one blood fluid through a living organism in a pulsatile manner of claim 1 wherein materials of construction for said pulsatile blood pumping system are selected from the group consisting of Teflon, titanium, pyrolytic carbon, Dacron, heparin, and polyurethane.

3. The method for circulating at least one blood fluid through a living organism in a pulsatile manner of claim 1 wherein said secondary vane is pivotally coupled to a carrier ring, so that said secondary vane is pivotal about a second pivotal axis perpendicular to the axis of rotation of said carrier ring causing said secondary vane to reciprocate between relatively open and closed positions as said secondary vane is rotated about said primary axis by said first shaft; the axis of rotation of said carrier ring being oriented at an oblique angle in relation to said primary axis of said first shaft.

4. The method for circulating at least one blood fluid through a living organism in a pulsatile manner of claim 3 further comprising a second shaft that extends into said interior of said housing opposite said first shaft, said second shaft having a spherical portion about which said primary vane rotates and wherein said carrier ring is rotatably carried on said spherical portion of said second shaft.

5. The method for circulating at least one blood fluid through a living organism in a pulsatile manner of claim 4 wherein said first shaft is rotatably coupled to said spherical portion of said second shaft to provide rigidity to the structure.

6. The method for circulating at least one blood fluid through a living organism in a pulsatile manner of claim 5 wherein said rotatable coupling is accomplished by an extension of a portion of said first shaft into said spherical portion of said second shaft.

7. The method for circulating at least one blood fluid through a living organism in a pulsatile manner of claim 5 wherein said rotatable coupling is accomplished by an extension of a portion of said spherical portion of said second shaft into said first shaft.

8. The method for circulating at least one blood fluid through a living organism in a pulsatile manner of claim 5 wherein a fluid channel is provided through the center of said first shaft, into said spherical portion of said second shaft, and out said second shaft, and further comprising the step of flowing a lubricant and/or coolant through the interior members of said pulsatile blood pumping system.

9. The method for circulating at least one blood fluid through a living organism in a pulsatile manner of claim 4 wherein seals are installed on both primary and secondary vanes to contact said housing during operation and wherein seals are installed on both primary and secondary vanes to contact said spherical portion of said second shaft during operation.

10. The method for circulating at least one blood fluid through a living organism in a pulsatile manner of claim 4 wherein said second shaft is adjustably mounted to said housing so that said second shaft can be oriented in various fixed positions, and further comprising;
an adjustable vane guide bearing member disposed within said housing, wherein the adjustable vane guide bearing member oscillates said secondary vane between relatively open and closed positions relative to said primary vane in response to rotation of said primary vane, varying the point during rotation of said first shaft and said primary vane at which said secondary vane reaches the relatively open and closed positions relative to said housing and said port opening so that communication of said port opening with said chamber is adjusted and therefore the fluid flow volume and/or direction is adjusted.

11. The method for circulating at least one blood fluid through a living organism in a pulsatile manner of claim 4 wherein clearances smaller than the diameter of a red blood cell are maintained between said carrier ring and said spherical portion or said housing.

12. The method for circulating at least one blood fluid through a living organism in a pulsatile manner of claim 4 wherein a fluid channel is provided through the center of said first shaft, into said spherical portion of said second shaft, and out said second shaft or out said first shaft, providing for a flow of a flushing medium through the interior members of said pulsatile blood pumping system.

13. The method for circulating at least one blood fluid through a living organism in a pulsatile manner of claim 12 wherein said flushing medium contains blood.

14. The method for circulating at least one blood fluid through a living organism in a pulsatile manner of claim 12 wherein said flushing medium contains blood plasma.

15. The method for circulating at least one blood fluid through a living organism in a pulsatile manner of claim 3 wherein said carrier ring is an exterior ring mounted in said wall of said housing.

16. The method for circulating at least one blood fluid through a living organism in a pulsatile manner of claim 1 wherein a flow pulse profile created by said pulsatile blood pumping system is adjusted through the use of a flow element that is resistive and/or capacitive in nature, said flow element being in communication with said pulsatile blood pumping system.

17. The method for circulating at least one blood fluid through a living organism in a pulsatile manner of claim 1 wherein the flow rate through said at least one discharge port opening of said pulsatile blood pumping system is adjusted based on feedback from sensors in said living organism.

18. The method for circulating at least one blood fluid through a living organism in a pulsatile manner of claim 17 wherein said sensor senses flow pulsations of at least one of the heart ventricles of said living organism and adjusts said rotational speed of said first shaft to coincide pulsatile flow of said pulsatile blood pumping system with said flow pulsations of said heart ventricle.

19. The method for circulating at least one blood fluid through a living organism in a pulsatile manner of claim 17 wherein said sensor senses flow demand of at least one of the heart ventricles of said living organism and adjusts said rotational speed of said first shaft to match said flow demand.

20. The method for circulating at least one blood fluid through a living organism in a pulsatile manner of claim 1 wherein the diameter of said generally spherical interior and the typical rotation rate of said primary shaft are sized to provide both a flow level and flow pulsation frequency that correspond with the flow and pulsation needs of the intended recipient.

21. The method for circulating at least one blood fluid through a living organism in a pulsatile manner of claim 1 wherein said pulsatile blood pumping system is implanted into the body of said living organism.

22. The method for circulating at least one blood fluid through a living organism in a pulsatile manner of claim 21 wherein said pulsatile blood pumping system is attached to the bones, muscles, sinews and/or internal organs of said living organism.

23. The method for circulating at least one blood fluid through a living organism in a pulsatile manner of claim 21 wherein the exposed surfaces in said pulsatile blood pumping system are porous to promote ingrowth of host cells to further anchor and provide biocompatibility within said living organism.

24. The method for circulating at least one blood fluid through a living organism in a pulsatile manner of claim 21 wherein a motor to rotate said first shaft is connected directly to said first shaft and fixedly mounted to said housing.

25. The method for circulating at least one blood fluid through a living organism in a pulsatile manner of claim 21 wherein a detached motor to rotate said first shaft is mechanically and/or electromagnetically linked to said first shaft.

26. The method for circulating at least one blood fluid through a living organism in a pulsatile manner of claim 21 wherein the power to rotate said first shaft is supplied transcutaneously.

27. The method for circulating at least one blood fluid through a living organism in a pulsatile manner of claim 26 wherein power to rotate said first shaft is supplied transcutaneously by radio frequency power transmitted across skin to a receiving coil.

28. The method for circulating at least one blood fluid through a living organism in a pulsatile manner of claim 26 wherein power to rotate said first shaft is transmitted via magnets coupled across skin surface.

29. The method for circulating at least one blood fluid through a living organism in a pulsatile manner of claim 26 wherein said pulsatile blood pumping system is implanted in chest cavity of living organism and said detached motor is implanted in abdominal cavity.

30. The method for circulating at least one blood fluid through a living organism in a pulsatile manner of claim 1 wherein said pulsatile blood pumping system is located outside the body of said living organism.

31. The method for circulating at least one blood fluid through a living organism in a pulsatile manner of claim 30 wherein a motor to rotate said first shaft is connected directly to said first shaft and fixedly mounted to said housing.

32. The method for circulating at least one blood fluid through a living organism in a pulsatile manner of claim 30 wherein a motor to rotate said first shaft is mechanically and/or electromagnetically linked to said first shaft, but physically detached from said housing.

33. The method for circulating at least one blood fluid through a living organism in a pulsatile manner of claim 30 wherein said at least one intake port opening and said at least one discharge port openings are accomplished by changeable port inserts.

34. The method for circulating at least one blood fluid through a living organism in a pulsatile manner of claim 33 wherein said changeable port inserts are eccentric in shape.

35. The method for circulating at least one blood fluid through a living organism in a pulsatile manner of claim 1 wherein at least one blood-contacting surface of said pulsatile blood pumping system is selected from the group consisting of heparin, acetylsalicylic acid and derivatives of any of the foregoing.

36. The method for circulating at least one blood fluid through a living organism in a pulsatile manner of claim 1 wherein at least one additive to blood flowing through said pulsatile blood pumping system is selected from the group consisting of heparin, acetylsalicylic acid and derivatives of any of the foregoing.

37. The method for circulating at least one blood fluid through a living organism in a pulsatile manner of claim 1 wherein at least one blood-contacting surface of the pulsatile blood pumping system is provided shaping to reduce shear forces on said blood fluid as it is circulated through said pulsatile blood pumping system.

38. The method for circulating at least one blood fluid through a living organism in a pulsatile manner of claim 37 wherein said shaping is provided on one of said vanes of said pulsatile blood pumping system.

39. The method for circulating at least one blood fluid through a living organism in a pulsatile manner of claim 38 wherein said shaping includes a groove in the surface of said vane wherein the direction of said groove near a given point on said vane is substantially aligned with the most direct path between said point on said vane and at least one of said ports of said pulsatile blood pumping system.

40. The method for circulating at least one blood fluid through a living organism in a pulsatile manner of claim 38 wherein said shaping includes constructing a first surface on a first of said vanes and a second surface on a second of said vanes, wherein said first and second surfaces are facing each other, in such a way that the first gap at a first point is greater than the second gap at a second point, wherein said first point is located on said first surface of said first vane and is nearer to a port than said second point which is also located on said first surface of said first vane, and wherein said first and second gaps are defined as the distance between respective said points and their nearest proximal points on said second surface of said second vane.

41. The method for circulating at least one blood fluid through a living organism in a pulsatile manner of claim 37 wherein said shaping includes a curvilinear transition between said generally spherical interior of said housing and an interior surface of one of said ports.

42. The method for circulating at least one blood fluid through a living organism in a pulsatile manner of claim 1 wherein a first fluid and a second fluid flow through the pulsatile blood pumping system.

43. The method for circulating at least one blood fluid through a living organism in a pulsatile manner of claim 42 wherein said first fluid is oxygen rich blood and said second fluid is oxygen poor blood.

44. The method for circulating at least one blood fluid through a living organism in a pulsatile manner of claim 42 wherein said first fluid is used to power said pulsatile blood pumping system and said second fluid is pumped.

45. The method for circulating at least one blood fluid through a living organism in a pulsatile manner of claim 42 wherein said first fluid and said second fluid are given two different flow rates.

46. The method for circulating at least one blood fluid through a living organism in a pulsatile manner of claim 45 said first fluid flows to, assists, or replaces the flow of the left ventricle of said living organism and said second fluid flows to, assists, or replaces the flow of the right ventricle of said living organism and wherein said first fluid is provided a higher flow rate than said second fluid.

47. The method for circulating at least one blood fluid through a living organism in a pulsatile manner of claim 45 wherein said two different flow rates are provided by rotating port openings to new fixed positions relative to said primary axis.

48. The method for circulating at least one blood fluid through a living organism in a pulsatile manner of claim 45 wherein said two different flow rates are provided by altering the shape or face angle of one or more vanes.

49. The method for circulating at least one blood fluid through a living organism in a pulsatile manner of claim 45 wherein said two different flow rates are provided by provision of a relatively one-way flow path between fluid chambers.

50. The method for circulating at least one blood fluid through a living organism in a pulsatile manner of claim 49 wherein said relatively one-way flow path between fluid chambers is accomplished via a flow path around a vane.

51. The method for circulating at least one blood fluid through a living organism in a pulsatile manner of claim 49 wherein said relatively one-way flow path between fluid chambers is accomplished via a flow path through a vane.

52. The method for circulating at least one blood fluid through a living organism in a pulsatile manner of claim 42 wherein a first fluid stream is provided communication with said at least one intake port opening and a second fluid stream is provided communication with said at least one discharge port opening, said first and second fluid streams providing flow to and from said pulsatile blood pumping system for said first fluid, and a third fluid stream is provided communication with a second intake port opening in said housing and a fourth fluid stream is provided communication with a second discharge port opening in said housing, said third and fourth fluid streams providing flow to and from said pulsatile blood pumping system for said second fluid.

53. The method for circulating at least one blood fluid through a living organism in a pulsatile manner of claim 1 wherein a first fluid stream is provided communication with said at least one intake port opening and a second intake port opening and a second fluid stream is provided communication with said at least one discharge port opening and a second discharge port opening, said first and second fluid streams providing flow of said blood fluid to and from said pulsatile blood pumping system.

54. The method for circulating at least one blood fluid through a living organism in a pulsatile manner of claim 1 wherein seals are provided between relatively moving surfaces in said pulsatile blood pumping system to limit the flow of said blood fluid between said relatively moving surfaces.

55. The method for circulating at least one blood fluid through a living organism in a pulsatile manner of claim 1 wherein said secondary vane is adjusted in weight or density so as to provide momentum near the relatively closed position with respect to said primary vane that balances the force exerted upon said secondary vane by the fluid pressurized in said at least one chamber.

56. The method for circulating at least one blood fluid through a living organism in a pulsatile manner of claim 1 wherein said volume of said at least one chamber approaches near zero with each cycle between relatively open and closed positions of said at least one chamber, for the substantially complete expulsion of said blood fluid from said at least one chamber with each cycle.

57. The method for circulating at least one blood fluid through a living organism in a pulsatile manner of claim 1 wherein said primary vanes and/or secondary vanes include magnetic portions that are acted upon by electromagnetic fields that are generated from within said housing wall or from outside of said housing wall, wherein said action causes said rotation of said primary vane and causes said oscillation of said secondary vanes.

58. The method for circulating at least one blood fluid through a living organism in a pulsatile manner of claim 57 wherein said external carrier ring includes magnetic portions that are acted upon by electromagnetic fields that are generated from within said housing wall or from outside of said housing wall, wherein said action causes said rotation of said primary vane and said oscillation of said secondary vanes.

59. The method for circulating at least one blood fluid through a living organism in a pulsatile manner of claim 1 wherein said at least one blood fluid is held temporarily in said at least one fluid chamber during the time interval in which said secondary vane has just approached the relatively open position with respect to said primary vane and before said secondary vane moves toward the relatively closed position with respect to said primary vane.

* * * * *